(12) United States Patent
Zhuo et al.

(10) Patent No.: US 8,512,678 B2
(45) Date of Patent: Aug. 20, 2013

(54) NON-INVASIVE, IN VIVO FLUORESCENT IMAGING OF THE NERVOUS SYSTEM IN WHOLE LIVING ANIMAL

(75) Inventors: Lang Zhuo, Singapore (SG); Gideon Ho, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 754 days.

(21) Appl. No.: 11/990,029

(22) PCT Filed: Sep. 27, 2006

(86) PCT No.: PCT/SG2006/000284
§ 371 (c)(1),
(2), (4) Date: Oct. 24, 2008

(87) PCT Pub. No.: WO2007/046774
PCT Pub. Date: Apr. 26, 2007

(65) Prior Publication Data
US 2009/0106851 A1 Apr. 23, 2009

Related U.S. Application Data

(60) Provisional application No. 60/727,843, filed on Oct. 19, 2005.

(51) Int. Cl.
*G01N 33/00* (2006.01)
(52) U.S. Cl.
USPC .................................. 424/9.6; 424/9.2; 800/3

(58) Field of Classification Search
None
See application file for complete search history.

(56) References Cited

U.S. PATENT DOCUMENTS

| | | | |
|---|---|---|---|
| 6,501,003 B1 * | 12/2002 | Messing et al. | 800/18 |
| 2003/0082515 A1 * | 5/2003 | Weiss et al. | 435/4 |
| 2010/0146646 A1 * | 6/2010 | Zhuo et al. | 800/3 |

FOREIGN PATENT DOCUMENTS

| | | |
|---|---|---|
| WO | 00/36106 A2 | 6/2000 |
| WO | 2005/078445 A1 | 8/2005 |

OTHER PUBLICATIONS

Zhu et al. Neuroscience Letters, 2004; 367:210-212.*
Okabe et al., FEBS Letters, 407(3):313-319 (1997).
Ho et al., Toxicology and Applied Pharmaceoloty, Academic Press, 221(1):76-85 (2007).
Yang et al., Proc. Natl. Acad. Sci. USA, 97(3), 1206-1211 (2000).
Extended European Patent Office search report for PCT/SG2006/000284 dated Nov. 19, 2008.

* cited by examiner

*Primary Examiner* — Doug Schultz
(74) *Attorney, Agent, or Firm* — Edwards Wildman Palmer LLP; Jeffrey D. Hsi

(57) ABSTRACT

A method is disclosed involving detecting the expression of a fluorescent protein of interest in an animal, wherein the animal is a transgenic animal having in its genome nucleic acid encoding said fluorescent protein operably linked to promoter nucleic acid from a protein that is normally expressed in the nervous system of the animal, the method comprising the step of non-invasively detecting fluorescence from said protein when expressed in said animal.

22 Claims, 18 Drawing Sheets x 10⁶ photons/sec/cm²/sr x 10⁹ photons/sec/cm²/sr

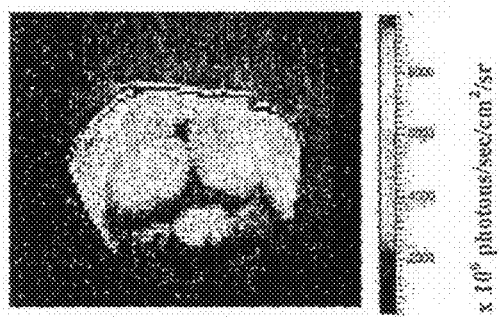
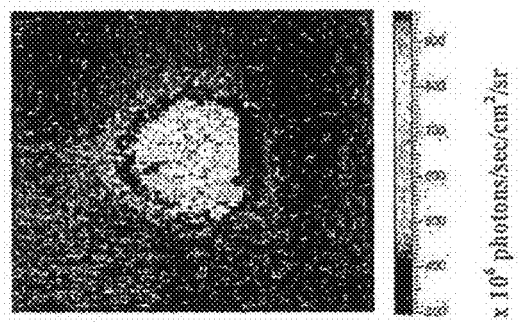
Figure 6A - Brain
Figure 6B - Liver

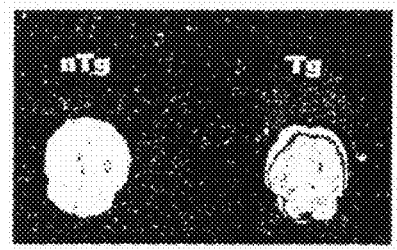
Figure 7A - Brain
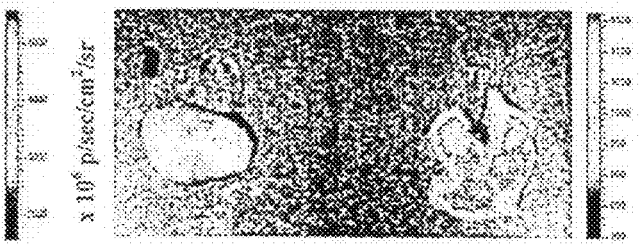
Figure 7B - Liver
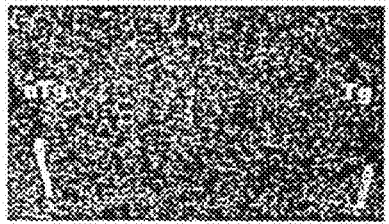
Figure 7C - Sciatic nerve
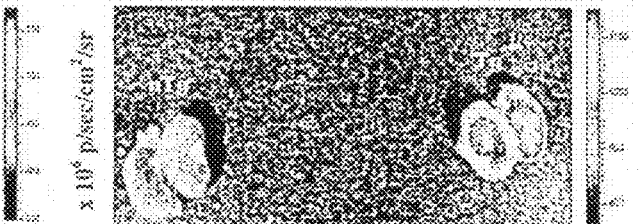
Figure 7D - Kidney

NON-INVASIVE, IN VIVO FLUORESCENT IMAGING OF THE NERVOUS SYSTEM IN WHOLE LIVING ANIMAL

FIELD OF THE INVENTION

The present invention relates to methods involving the non-invasive imaging of a fluorescent protein expressed in a transgenic animal.

BACKGROUND TO THE INVENTION

Parkinson's disease (PD) is the second most common neurodegenerative disorder after Alzheimer's dementia. It is estimated that more than one million individuals in the United States of America alone are affected with this disabling disease and more than 50,000 new cases arise each year (Fahn and Przedborski, 2000). A progressive, age-related, neurodegenerative disease characterized by bradykinesia, resting tremor, rigidity and gait disturbance, PD is also characterized by a massive progressive destruction of dopaminergic neurons in the substantia nigra. Like many other neurodegenerative diseases, PD presents itself mainly as a sporadic condition, meaning in the absence of any genetic linkage, but in rare instances, PD can also arise as a simple Mendelian trait, linked to defects in a variety of genes.

Although clinically and pathologically sporadic and familial PD may differ on several significant aspects they all share the same biochemical brain abnormality, namely the dramatic depletion in brain dopamine (Dauer and Przedborski, 2003). The reason why PD patients exhibit low levels of brain dopamine stems from the degeneration of the nigrostriatal dopaminergic pathway, which is comprised of dopaminergic neurons whose cell bodies are located in the substantia nigra and whose projecting axons and nerve terminals are found in the striatum (Vila and Przedborski, 2004).

The best-characterized model of PD has been developed by using the neurotoxin, MPTP (Bloem et al., 1990, Flint Beal, 2001). The discovery of MPTP occurred in 1982 when a group of drug addicts in California developed acute onset of severe Parkinsonism. Investigation revealed that the syndrome was caused by self-administration of a synthetic heroin analogue that had been contaminated by a by-product, MPTP during manufacture. MPTP administration was subsequently shown to model PD in both mice and primates. MPTP is highly lipophilic and it readily crosses the blood-brain barrier. It is then converted into its active metabolite, 1-methyl-4-phenylpyridinium ($MPP^+$) by monoamine oxidase B which is then taken up by high-affinity dopamine and noradrenaline uptake systems and is consequently accumulated within mitochondria of nigrostriatal dopaminergic cells. This can lead to a number of deleterious effects on cellular function, resulting in neuronal cell death (Tatton and Kish, 1997, Tanji et al., 1999). In mice, 2'-$CH_3$-MPTP is a more potent neurotoxin than conventional MPTP showing severe histopathological changes including swelling of cytoplasm, interstitial edema, depletion of dopaminergic neurons with reactive microglial proliferation and gliosis (Abdel-Wahab, 2005).

While most of the research on PD has been conducted with a focus on adults, some reports convincingly demonstrate that systemic MPTP injection into neonatal mice results in permanent brain damage which can be traced in adulthood. The fact that developing brain is vulnerable to MPTP damage as well deserves further investigation.

In addition to MPTP, a number of other chemicals have also been reported to cause neuronal damages in various regions of adult mouse brain. These chemicals include a long list of structurally and functionally diverse compounds, ranging from industrial toxic compounds, agricultural pesticides, to food additives. Once again, most of the neurotoxicity studies conducted thus far have been based on adult models. However it is important to note that the developing brain with less intact blood-brain-barrier is much more vulnerable to damage caused by known neurotoxins, and more critically the damage inflicted cannot be fully and correctly compensated by the developing brain. Therefore the importance of testing chemicals for their potential neurotoxicity in developing brain cannot be over-emphasized, especially in dealing with the issue of silent neurotoxicity (i.e., early exposure to neurotoxicants, but without clinical symptoms until adulthood). This was further exacerbated by the US Environmental Protection Agency's Developmental Neurotoxicity Testing Guideline (DNTG). More recently the European Commission adopted a proposal for a new European Union regulatory framework to test all chemicals through a rigorous regime with estimates of the new measure costing up to seven billion Euros and taking at least ten years to implement.

Glial fibrillary acidic protein (GFAP), an intermediate filament protein expressed predominately in the astrocytes of the central nervous system (CNS), has been proposed by O'Callaghan (O'Callaghan, 1988) to be an early and sensitive biomarker for monitoring neuronal damages in adult rodent brains caused by various neurotoxic agents, including 1-methyl-4-phenyl-1,2,3,6-tetrahydropyridine (MPTP) (Reinhard et al., 1988, Araki et al., 2001, Chen et al., 2002, Fields and Stevens-Graham, 2002, Kurosaki et al., 2004). An upregulation of GFAP expression has been correlated with increased neurological damage. The traditional methods employed to analyze endogenous GFAP expression include predominantly immunocytochemistry, Northern blot, Western blot and ELISA (O'Callaghan, 1991, Eng et al., 2000).

The GFAP basal promoter consists of a TATA and a CAAT box. Enhancer and silencer sequences are found between −250 and −80 bp and between −1980 and −1500 bp. These positive control regions contain consensus sequences for many transcription factors including a cAMP response element and binding sites for the Sp-1, NF-1, AP-1 and AP-2 transcription factors. Tissue specificity is conferred by a human GFAP consensus sequence located in the −1980 to −1500 bp region.

Reactive gliosis (astrogliosis) occurs in response to almost any insult, physical or chemical, to the central nervous system (CNS) and is characterized by hypertrophy of the astrocyte cell body and its processes, accompanied by an increase in expression of GFAP. Reactive gliosis is accompanied by an up-regulation of GFAP. A similar increase in GFAP occurs following traumatic and toxic injuries to the peripheral nervous system.

With the advancement in mouse transgenics and the availability of novel reporter genes, several reporter genes, including beta-galactosidase (lacZ), green fluorescent protein (GFP), and luciferase (LUC) have been introduced into transgenic mice under the control of the GFAP promoter and proved to be useful surrogates for studying the GFAP transcriptional activity during gliosis in vivo (Brenner et al., 1994, Zhuo et al., 1997, Zhu et al., 2004).

WO 00/02997 and U.S. Pat. No. 6,501,003 describe the generation of a transgenic mouse expressing green fluorescent protein in glial cells. The authors describe the in vitro detection of fluorescence in optic nerve, brain, retina, sciatic nerve and cornea either in whole mounted tissue or sections thereof.

SUMMARY OF THE INVENTION

For the purpose of facilitating the studies on the developmental aspects of PD and neurotoxicity, the inventors established a non-invasive system, comprising a GFAP-GFP transgenic mouse model and a commercially available imaging system, which permits the study of various aspects of neurological disease, damage and toxicity in living animals. This system also enables the screening of a large number of chemicals for their neurotoxic risk to the developing central nervous system in an efficient manner.

By using a transgenic animal that expresses a fluorescent protein under the control of a promoter from a protein that is normally expressed in the nervous system of an animal the inventors have now shown that fluorescence detection in whole, live transgenic animals can be used to monitor the effect of stimuli and test substances on the expression of the fluorescence protein from that promoter. This represents a significant improvement over the state of the art as it enables real-time, or close to real-time, monitoring of the effects of test substances on the intact animal nervous system in vivo.

At its most general the present invention relates to methods involving the non-invasive detection of fluorescence from a fluorescent protein expressed in a transgenic animal.

According to a first aspect of the present invention a method is provided which involves detecting the expression of a fluorescent protein of interest in an animal, wherein the animal is a transgenic animal having in its genome nucleic acid encoding said fluorescent protein operably linked to promoter nucleic acid from a protein that is normally expressed in the nervous system of the animal, the method comprising the step of non-invasively detecting fluorescence from said protein when expressed in said animal.

Accordingly, the use of a transgenic animal having in its genome nucleic acid encoding said fluorescent protein operably linked to promoter nucleic acid from a protein that is normally expressed in the nervous system of the animal in a method of non-invasively detecting fluorescence from said protein when expressed in said animal is also provided.

The method is preferably for studying the effect of administration of a test substance, or application of a test stimulus, to a said animal, wherein the method comprises the step of administering said test substance, or stimulus, to a said animal prior to a step of non-invasive detection of fluorescence. Preferably, the method is for studying the effect of the test substance, or stimulus, on the neurological condition of the animal. The methods of the present invention may therefore provide methods for screening neurological modulators.

The method preferably comprises the step of comparing fluorescence detected from a control animal in the absence of administration of said test substance with the fluorescence detected from a said transgenic animal following administration of said test substance to the transgenic animal.

Detection of fluorescence in the absence of administration of a test substance enables one to provide a control value, or base reading, e.g. for autofluorescence, which may be used together with detection of fluorescence following administration of the test substance to calculate relative fluorescence values for standardisation purposes. The control value may be determined in a transgenic animal, e.g. of the same kind in which the test substance is to be tested, or a non-transgenic animal. The animals will preferably be of the same kind, e.g. mice, and most preferably the same strain. A placebo, e.g. saline, may be administered to the control animal for the purpose of obtaining control values.

Accordingly, in one preferred arrangement the method comprises the steps of:
(i) non-invasively detecting fluorescence in a said transgenic animal before administration of the test substance to provide a control;
(ii) non-invasively detecting fluorescence in the same animal after administration of the test substance; and
(iii) comparing the fluorescence detected in (i) with the fluorescence detected in (ii).

And in an alternative preferred arrangement the method comprises the steps of:
(i) non-invasively detecting fluorescence in a first animal to provide a control;
(ii) administering a test substance to a second transgenic animal followed by non-invasively detecting fluorescence in that animal; and
(iii) comparing the fluorescence detected in (i) with the fluorescence detected in (ii).

The first animal may be transgenic or non-transgenic.

In one preferred arrangement the methods of the present invention are provided for determining the neurotoxicity of the test substance.

In another preferred arrangement the methods of the present invention are provided for testing the ability of the test substance to facilitate the treatment of, or to modulate, neurological damage.

Accordingly, the method may comprise the steps of:
(i) inducing neurological damage in a said transgenic animal;
(ii) non-invasively detecting fluorescence in said neurologically damaged animal from (i) prior to administration of the test substance to provide a control;
(iii) non-invasively detecting fluorescence in the same animal from (ii) after administration of the test substance; and
(iv) comparing the fluorescence detected in (ii) with the fluorescence detected in (iii).

Alternatively, the method may comprise the steps of:
(i) inducing neurological damage in a first animal and non-invasively detecting fluorescence in the neurologically damaged animal to provide a control;
(ii) inducing neurological damage in a second transgenic animal and administering the test substance to that animal followed by non-invasively detecting fluorescence in that animal; and
(iii) comparing the fluorescence detected in (i) with the fluorescence detected in (ii).

The first animal may be transgenic or non-transgenic.

The neurological damage may be any damage or injury to the nervous system, however induced. Preferably, the damage is to the central nervous system, more preferably to the brain.

The neurological damage may be reactive gliosis.

The neurological damage may be chemically induced by administration of a selected chemical to the animal, for example neurotoxins such as MPTP, 2'-$CH_3$-MPTP, 6-hydroxydopamine (6-OHDA), Kainic acid (KA), Trimethylin, pesticides such as Chlorpyrifos (CPF), fungicides such as Manganese ethylenebisdithiocarbamate (Maneb or MB), insecticides such as rotenone, herbicides such as Paraquat (N,N',-dimethyl-4-4'-bipiridinium), organochlorines such as Polychlorinated biphenyls (PCBs), food additives such as monosodium glutamate (MSG), industrial chemicals such as 3,3'-Iminodipropionitrile (IDPN), Toluene (methylbenzene). The person skilled in the art is capable of selecting a suitable amount of the chemical for administration to the animal and of formulating a suitable dosage regimen in order to induce the neurological damage. By way of example, single or multiple (e.g. 2, 3, 4, 5 or more) doses of the selected chemical may be administered. Multiple doses may be administered at predetermined time intervals, e.g. 1, 2, 3, 4, 5, 6 or more hours. Also by way of example, each dose may be chosen from 2, 4, 6, 7, 8, 12 or 14 mg/kg.

Alternatively, the neurological damage may be induced by the application of physical force, e.g. a crush injury, to the head and/or neck and/or back of the animal. The neurological damage may be induced by decreasing the supply of oxygen to the animal's nervous system leading to stroke and/or cerebral ischaemia. Other means of inducing neurological damage may include environmental stimuli, mechanical force, exposure to viral particles or genetic factors.

In preferred arrangements the neurological damage is such as to provide an animal model of a selected disease. For example, the disease may be chosen from Parkinson's Disease, Alzheimer's Disease or Huntington's Disease. An animal model of Parkinson's Disease may be chemically induced by administration of MPTP (1-methyl-4-phenyl-1,2,3,6-tetrahydropyridine) or 2'-$CH_3$-MPTP.

In further preferred arrangements the methods of the present invention are provided for testing the ability of a test substance to facilitate treatment of a nervous system disease.

Accordingly, in one preferred arrangement the method comprises the steps of:
 (i) providing a said transgenic animal, wherein the animal is also an animal model of a nervous system disease;
 (ii) non-invasively detecting fluorescence in said animal from (i) prior to administration of the test substance to provide a control;
 (iii) non-invasively detecting fluorescence in the same animal from (ii) after administration of the test substance; and
 (iv) comparing the fluorescence detected in (ii) with the fluorescence detected in (iii).

Alternatively, the method may comprise the steps of:
 (i) providing first and second animals, wherein both animals are animal models of a nervous system disease;
 (ii) in a first animal from (i) non-invasively detecting fluorescence in the animal to provide a control;
 (iii) in a second transgenic animal from (i) administering the test substance to that animal followed by non-invasively detecting fluorescence in that animal; and
 (iv) comparing the fluorescence detected in (ii) with the fluorescence detected in (iii).

The first animal may be transgenic or non-transgenic.

In further preferred arrangements the methods of the present invention are provided for testing a treatment for a nervous system disease.

Accordingly, in one preferred arrangement the method comprises the steps of:
 (i) providing a said transgenic animal, wherein the animal is also an animal model of a nervous system disease;
 (ii) non-invasively detecting fluorescence in said animal from (i) prior to applying the treatment to provide a control;
 (iii) non-invasively detecting fluorescence in the same animal from (ii) after applying the treatment; and
 (iv) comparing the fluorescence detected in (ii) with the fluorescence detected in (iii).

Alternatively, the method may comprise the steps of:
 (i) providing first and second animals, wherein both animals are animal models of a nervous system disease;
 (ii) in a first animal from (i) non-invasively detecting fluorescence in the animal to provide a control;
 (iii) in a second transgenic animal from (i) applying the treatment to that animal followed by non-invasively detecting fluorescence in that animal; and
 (iv) comparing the fluorescence detected in (ii) with the fluorescence detected in (iii).

The first animal may be transgenic or non-transgenic.

Preferably, the nervous system disease is a nervous system tumor, which may be chosen from glioma, medulloblastoma, meningioma, neurofibroma, ependymoma, Schwannoma, neurofibrosarcoma, astrocytoma, oligodendroglioma. Animal models of nervous system tumor may be generated by tumor xeongraft techniques well known to those of skill in the art.

Suitably, the applied treatment may involve the application of radiotherapy, e.g. X-rays or γ-rays, or a chemotherapeutic drug.

Where the methods of the present invention involve the use of animals having neurological damage or nervous system disease, the claimed invention may optionally omit the step of inducing said disease and/or damage in the animal, in which case the methods do not relate to the generation of such animals, but to their use.

The animals (transgenic and non-transgenic) are preferably non-human mammals e.g. rabbit, guinea pig, rat, mouse or other rodent (including any animal in the order Rodentia), cat, dog, pig, sheep, goat, cattle, horse, non-human primate; or any other non-human vertebrate organism. Most preferably, the animals (transgenic and non-transgenic) are mice. In any given method the same type of animal, e.g. mouse, is preferably used as the control and test animal. The animals may differ in that one may be transgenic and the other non-transgenic, although the test animal will always be transgenic. Both control and test animals may be transgenic.

The promoter nucleic acid is from a protein that is normally expressed in the nervous system of the animal. Whilst the nucleic acid sequence of the promoter may be modified as compared to the wild type, e.g. by substitution, addition, deletion (truncation), insertion or replacement of nucleotides, the promoter nucleic acid is characterised by the ability to regulate nervous system expression of a protein when operably linked to nucleic acid encoding that protein. Most preferably, the promoter retains a corresponding ability to regulate transcription (and thereby protein expression) in nervous system tissue as compared to the wild type promoter.

In this specification the term "operably linked" may include the situation where a selected nucleotide sequence (e.g. protein coding sequence) and regulatory nucleotide sequence (e.g. promoter) are covalently linked in such a way as to place the expression of the selected nucleotide sequence under the influence or control of the regulatory sequence. Thus a regulatory sequence is operably linked to a selected nucleotide sequence if the regulatory sequence is capable of effecting transcription of a protein coding sequence which forms part or all of the selected nucleotide sequence. Where appropriate, the resulting transcript may then be translated into a desired protein or polypeptide.

Most preferably, the promoter is a GFAP promoter. GFAP promoter sequences are well known to those of skill in the art. Examples of GFAP promoters and their use in constructing GFAP transgenes, where the expression of a protein is placed under the control of a GFAP transcription control region, are described in Brenner and Messing, Methods: A Companion to Methods in Enzymology 10, 351-364 (1996) which is incorporated herein by reference.

The fluorescent protein may be any fluorescent protein.

Many suitable fluorescent proteins are known to those skilled in the art such as green, blue, cyan, yellow, orange and red fluorescent proteins. Most preferably, the fluorescent protein is a green fluorescent protein (GFP) such as hGFP-S65T green fluorescent protein gene, EGFP-1 green fluorescent gene, or EYFP-1 green fluorescent protein gene, or any variant thereof having mammalian compatible or humanized sequences (e.g. codon modification which renders the construct more compatible with mammalian ribosome translation) and a mutation increasing its light emission coefficient.

In this specification a "transgenic animal" includes animals in which nucleic acid encoding a fluorescent protein operably linked to promoter nucleic acid from a protein that is normally expressed in the nervous system of the animal has been introduced into the organism's genome through the use of recombinant nucleic acid technology. Techniques for generation of transgenic non-human mammals are well-known to persons skilled in the art.

In methods according to the present invention the animals are preferably neonatal, i.e. of less than four weeks age from birth. More preferably, the neonatal animals are less than 3 weeks old from birth, more preferably less than 14 days old from birth. Optionally, the neonatal animals may be between 1 and 14 days old from birth, preferably from 1-7 days old from birth, alternatively from 7-14 days old from birth. Neonatal animals may be any one of 1, 2, 3, 4, 5, 6, 7, 8, 9, 10, 11, 12, 13, 14, 15, 16, 17, 18, 19, 20, 21, 22, 23, 24, 25, 26, 27 or 28 days old from birth.

By using neonatal mice, the development of the nervous system may be monitored, and particularly the effect of test substances on the developing nervous system.

In methods according to the present invention fluorescence is detected by non-invasive fluorescence imaging. The imaging technique is non-invasive in that the animal is imaged from the exterior of the animal and no surgical intervention is involved in the detection of fluorescence. The animal thus remains whole and intact during imaging. Although the animal may optionally be anaesthetised for the purpose of detecting fluorescence, the animal is preferably living during fluorescence detection. Suitable apparatus and techniques for non-invasive fluorescence imaging are known to persons of skill in the art, such as the IVIS® Imaging System 100 Series (Xenogen Corp., Alameda, USA).

Fluorescence detection may be carried out at any convenient time point before or after administration of the test substance in order to establish control or test values. Often, it will be preferred to perform a series of post-administration detections in order to monitor the change in fluorescence over time. Optionally a control reading may be taken at each corresponding time point, e.g. from an animal given a placebo instead of the test substance. For example, detection may be carried out immediately or shortly before administration of the test substance, e.g. up to 1 hour before, followed by regular detection thereafter, e.g. at hourly intervals. Alternatively, detection after administration of the test substance may be carried out daily, twice daily, three times daily or four times daily and for as many days as the investigator desires, e.g. 1, 2, 3, 4, 5 or more days.

Detection of fluorescence is preferably from a region of interest (ROI) on the animal. The ROI is preferably an area of interest to the investigator. A preferred ROI is the central nervous system or a part thereof, most preferably the brain or a part thereof. Optionally the ROI may exclude one or more of the optic nerve, retina, sciatic nerve, cornea or any part of the mammalian eye. A corresponding ROI is preferably used for the purpose of comparing fluorescence detection in control and test animals.

Detection of fluorescence in control animals provides a base reading of animal autofluorescence. A direct comparison between the base reading and test readings may be made. However, in one particularly preferred arrangement a relative fluorescence (RF) value may be calculated and used for comparison purposes. The RF value is preferably calculated as the ratio between total fluorescence detected from the ROI at a time point post-administration of the test substance in the transgenic mouse and tissue autofluorescence detected from the ROI in the control mouse (optionally at the same time point, e.g. where a placebo was given), which may be transgenic or non-transgenic.

In preferred arrangements, an increase in fluorescence detected indicates an increase in neurological damage, neurotoxicity or nervous system disease progression. In other arrangements a decrease in fluorescence may indicate an increase in neurological damage.

The detection of fluorescence may be quantitative and/or qualitative.

In this specification reference to the nervous system of an animal may include the central nervous system or peripheral nervous system. More preferably, it is the central nervous system, still more preferably the brain and/or spinal cord.

The test substance may be any substance, material, composition, chemical compound, drug, medicament, protein, peptide, antibody, nucleic acid, small molecule, industrial chemical, pesticide, food additive or preservative. The test substance may be a material or tissue that is surgically implanted into the test animal, e.g. an artificial biomaterial.

The methods of the invention may be used to monitor the effect of the test substance on the animal and may be used for:
 formulating a disease diagnosis;
 formulating a disease prognosis;
 monitoring and/or quantifying chemical-induced gliosis and/or lesion development in the brain;
 diagnosis and prediction of the development of Parkinson's Disease;
 the development of therapeutics, e.g. anti-Parkinson's Disease drugs or gene therapies;
 monitoring and quantifying neurotoxicant induced gliosis and/or lesion development in the brain;
 measuring the developmental neurotoxicity of artificial biomaterials used for implant and tissue engineering;
 measuring the developmental neurotoxicity of drug compounds during pharmaceutical development;
 measuring the pharmacokinetic and/or pharmacodynamic properties of the test substance.

The invention includes the combination of the aspects and preferred features described except where such a combination is clearly impermissible or expressly avoided.

Aspects and embodiments of the present invention will now be illustrated, by way of example, with reference to the accompanying figures. Further aspects and embodiments will be apparent to those skilled in the art. All documents mentioned in this text are incorporated herein by reference.

DETAILED DESCRIPTION OF THE PREFERRED EMBODIMENTS

In the preferred embodiment of the invention the genome of the transgenic animal has nucleic acid encoding a green fluorescent protein operably linked to a GFAP promoter.

Transgenic mice of this kind have been previously described in Zhou et al 1997 Developmental Biology 187, 36-42, and WO 00/02997 and U.S. Pat. No. 6,501,003, each specifically incorporated by reference in their entirety. The GFAP promoter drives expression of the fluorescent protein in glial cells, such as astrocytes, Schwann cells and Mueller cells.

The transgenic mouse was engineered to express a transgene encoding a humanized green fluorescent protein gene operably linked to a glial fibrillary acidic protein promoter. In the transgenic mouse the green fluorescent protein is upregulated specifically in glial cells such as astrocytes, Schwann cells, and Mueller cells in response to neurological damage.

The transgenic mouse was engineered by insertion of a genetic construct into the pronucleus of a mammalian zygote, and allowing stable genomic integration to occur naturally. The zygote was then transferred to a receptive uterus, and allowed to develop to term.

The genetic construct comprises a full length glial fibrillary acidic protein promoter to provide glial cell specific expression. The promoter is located 5' of, and is operably linked to, a mutant gene encoding green fluorescent protein, and a segment of DNA located 3' of the green fluorescent protein encoding gene containing signal sequences for proper RNA splicing and polyadenylation.

Non-invasive imaging of animals was performed to establish control values for autofluorescence and test values following administration of the test substance—e.g. see Example 1 Materials and Methods.

An increase in fluorescence indicated an increase in neurotoxicity or neurological damage.

BRIEF DESCRIPTION OF THE FIGURES

Embodiments and experiments illustrating the principles of the invention will now be discussed with reference to the accompanying figures in which.

Figure 1A:
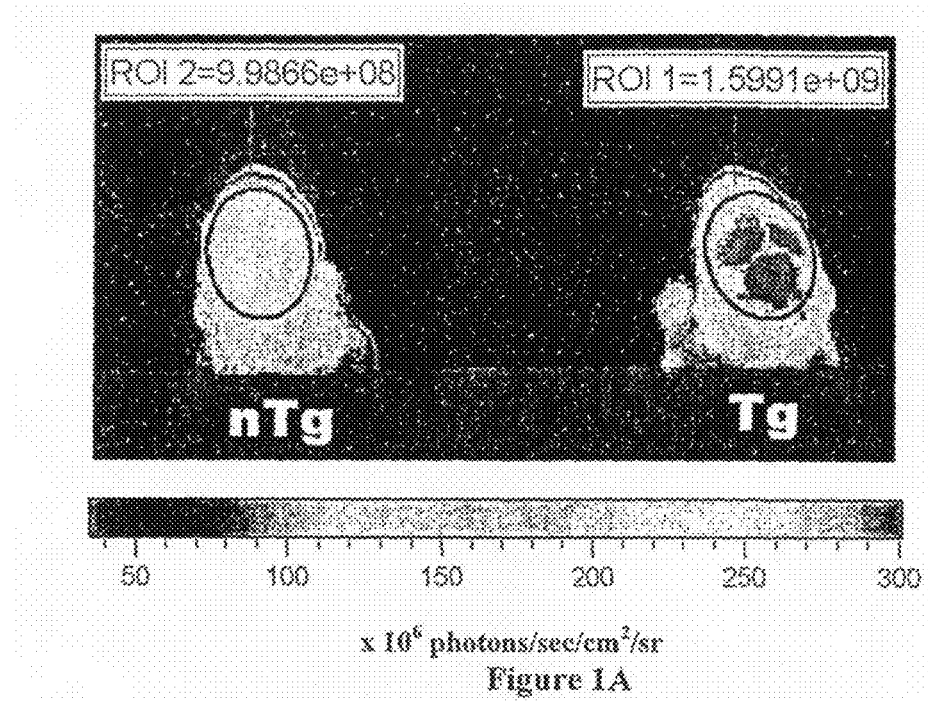
FIG. 1.

(A) In vivo fluorescent images of a pair of transgenic and non-transgenic neonatal mouse. Total GFP fluorescence was detected from the ROI in the brain of the transgenic mouse and tissue autofluorescence from the non-transgenic mouse.

Quantitation of the radiance in photons/sec/cm$^2$/sr using the Living Image® software (Xenogen Corp.). (B) Ex vivo fluorescent images of the brain of a pair of transgenic and non-transgenic neonatal mouse.

FIG. 2.

Non-invasive in vivo neural imaging of GFAP-GFP transgenic neonatal mice. Mice were treated using saline (control) and 12 mg/kg of 2'-CH$_3$-MPTP and imaged as described in the text. Mice at 0 hr were imaged prior to administration of 2'-CH$_3$-MPTP. Acquisition time for fluorescence imaging was 10 s. For each pair of mice, the transgenic mouse is positioned on the right and the non-transgenic mouse on the left.

FIG. 3.

Comparison between 2'-CH$_3$-MPTP-treated and control groups (mean±SEM, n=5) of the ratio between the total GFP fluorescence detected from the ROI in transgenic mice and the tissue autofluorescence from the ROI in non-transgenic mice expressed as relative fluorescence (RF). The RF is normalized to 0 hr. * indicate statistical significance of 2'-CH$_3$-MPTP treated group versus control group (P<0.05). ** (P<0.01), compared with control group. Student's two-tailed paired t-test.

FIG. 4.

Confocal images of GFAP immunostaining in the hippocampus showing (A) no GFP expression in the nTg mice, bar=100 μm; (B, C) increase in GFP expression 6 hr after 2'-CH$_3$-MPTP treatment in the Tg mice using a 10× objective lens, bar=200 μm; (D, E) using a 40× objective lens, bar=50 μm. Cell processes localization of GFAP immunopositive astrocytes and endogenous GFAP-GFP transgene-marked astrocytes are indicated by arrows.

FIG. 5.

Confocal images of TH immunostaining in the substantia nigra compact (SNC) showing (A) no GFP expression in the nTg mice, bar=100 μm; (B, C) increase in GFP expression 6 hr after 2'-CH$_3$-MPTP treatment in the Tg mice using a 20× objective lens, bar=100 μm; (D, E) using a 40× objective lens, bar=50 μm.

FIG. 6.

In vivo Skin flap imaging of GFAP-GFP adult mice. (A) Brain; (B) Liver.

FIG. 7.

Ex vivo imaging of both transgenic (Tg) and non-transgenic (nTg) mice (A) brain, (B) Liver, (C) Sciatic Nerve, (D) Kidney.

FIG. 8.

Non-invasive in vivo neural imaging of GFAP-GFP transgenic neonatal mice. Mice were treated using saline (control) and 8 mg/kg of MPTP and imaged as described in the text. Mice at 0 hr were imaged prior to administration of MPTP. Acquisition time for fluorescence imaging was 10 s. For each pair of mice, the transgenic mouse is positioned on the right and the non-transgenic mouse on the left.

FIG. 9.

Comparison between MPTP-treated at 1×12 mg/kg, 4×8 mg/kg and the respective control groups (mean±SEM, n=5) of the ratio between the total GFP fluorescence detected from the ROI in transgenic mice and the tissue autofluorescence from the ROI in non-transgenic mice expressed as relative fluorescence (RF). The RF is normalised to 0 hr. * indicate statistical significance of MPTP-treated group versus control group (P<0.01). Student's two-tailed paired t-test.

FIG. 10.

(A) Effect of MPTP (4×8 mg/kg) on GFAP and GFP expression investigated using Western Blot. Lane (a) untreated, transgenic mouse. Lane (b) 24 hours after MPTP treatment, transgenic mouse. Lane (c) untreated, non-transgenic mouse. Lane (d) 24 hours after MPTP treatment, non-transgenic mouse.

(B) Effect of MPTP on GFAP and GFP expression investigated using IVIS imaging of Western Blot membrane. Units are in p/sec/cm$^2$/sr .

FIG. 11.

(A) Effect of MPTP (4×8 mg/kg) on GFAP gene expression in transgenic and non-transgenic mice using real-time RT-PCR. Results were normalized values against control (untreated) to obtain fold enhancement±S.E.M. * p<0.1; n=4; two-tailed sample t-test.

(B) Effect of MPTP (4×8 mg/kg) on GFP gene expression in transgenic mice using real-time RT-PCR. Results were normalized values against control (untreated) to obtain fold enhancement±S.E.M.

FIG. 12.

Endogenous GFP in different regions if the neonatal brain before and after MPTP administration (4×8 mg/kg).

FIG. 13.

Results of IHC anti-TH (Substantia nigra compacta) in 8-10 week old adult transgenic mice.

FIG. 14.

(A) Effect of MPTP (1×12 mg/kg) on GFAP and GFP expression investigated using Western Blot. Lane (a) untreated, transgenic mouse. Lane (b) 6 hours after MPTP treatment, transgenic mouse. Lane (c) untreated, non-transgenic mouse. Lane (d) 6 hours after MPTP treatment, non-transgenic mouse.

(B) Effect of MPTP on GFAP and GFP expression investigated using IVIS imaging of Western Blot membrane. Units are in p/sec/cm$^2$/sr.

FIG. 15.

Effect of MPTP (1×12 mg/kg) on GFAP and GFP gene expression in transgenic mice using real-time RT-PCR. Results were normalized values against control (untreated) to obtain fold enhancement±S.E.M. * p<0.01 ** p<0.001; n=5; two-tailed sample t-test.

FIG. 16.

Non-invasive in vivo neural imaging of GFAP-GFP transgenic neonatal mice. Mice were treated using saline (control) and 2 mg/kg of KA and imaged as described in the text. Mice at 0 hr were imaged prior to administration of KA. Acquisition time for fluorescence imaging was 10 s. For each pair of mice, the transgenic mouse is positioned on the right and the non-transgenic mouse on the left

FIG. 17.

Comparison between KA-treated at 2 mg/kg and control groups (mean±SEM, n=4) of the ratio between the total GFP fluorescence detected from the ROI in transgenic mice and the tissue autofluorescence from the ROI in non-transgenic mice expressed as relative fluorescence (RF). The RF is normalised to 0 hr. * indicate statistical significance of KA-treated group versus control group (P<0.05). ** (P<0.01), compared with control group. Student's two-tailed paired t-test.

FIG. 18.

(A) Effect of KA (1×2 mg/kg) on GFAP and GFP expression investigated using Western Blot. Lane (a) untreated, transgenic mouse. Lane (b) 6 hours after KA treatment, transgenic mouse. Lane (c) untreated, non-transgenic mouse. Lane (d) 6 hours after KA treatment, non-transgenic mouse.

(B) Effect of KA on GFAP and GFP expression investigated using IVIS imaging of Western Blot membrane. Units are in p/sec/cm$^2$/sr.

FIG. 19.

Effect of KA (1×2 mg/kg) on GFAP and GFP gene expression in transgenic mice using real-time RT-PCR. Results were normalized values against control (untreated) to obtain fold enhancement±S.E.M. * p<0.05 ** p<0.01; n=5; two-tailed sample t-test.

FIG. 20.

Confocal images of GFAP immunostaining in the hippocampus area showing CA1 (A, B); CA2 and CA3 (C, D). (B, D) shows increase in GFP expression 6 hr after KA treatment in the transgenic (Tg) mice using a 20× objective lens as compared to the hippocampus area of the untreated mice (A, C). bar=50 µm using a 20× objective lens. Cell processes localization of GFAP immunopositive astrocytes and endogenous GFAP-GFP transgene-marked astrocytes are indicated by arrows.

DETAILED DESCRIPTION OF THE INVENTION

Specific details of the best mode contemplated by the inventors for carrying out the invention are set forth below, by way of example. It will be apparent to one skilled in the art that the present invention may be practiced without limitation to these specific details.

EXAMPLE 1

In an attempt to develop a non-invasive fluorescent imaging system for the screening purpose as stated above, we used 2'-CH$_3$-MPTP as a model neurotoxicant in the neonatal brain of transgenic GFAP-GFP mice, which was previously created by Zhuo et al., 1997. Here we showed that the transgenic GFAP-GFP mouse model, when coupled with an appropriate in vivo optical imaging system, can reliably detect the GFAP-GFP signature in transgenic mice and quantify its up-regulation in response to MPTP induction in a dose- and time-dependent manner. Such non-invasive optical fluorescent system with a reasonable throughput should find broad applications in studying Parkinsonism and other neurodegenerative diseases, developmental neurotoxicology and in preclinical compound screening.

Materials and Methods

Transgenic GFAP-GFP Mice

The generation and genotyping of the transgenic GFAP-GFP mice were done as previously described (Zhuo et al., 1997). Neonatal mice of FVB/N background at 4 days of age, weighing 2.0 g-2.5 g were used in the present study. Animal husbandry was provided by National University of Singapore animal holding unit facility. The experimental protocol covering the current study was approved by the Institutional Animal Care and Use Committee.

Neurotoxicant and Dosing

The test compound 2'-CH$_3$-MPTP, a more potent analog of the conventional MPTP (Abdel-Wahab, 2005), was purchased from (Sigma-Aldrich, M-103). The neonatal mice received a single subcutaneous (sc) injection of 2'-CH$_3$-MPTP (12 mg/kg in saline) at 0 hour. Saline was used as a vehicle for the control group. Neural imaging was subsequently performed at 2 hr, 4 hr, 6 hr and 8 hr post-treatment.

In vivo Neural Imaging

Non-invasive imaging was conducted using an IVIS Imaging System 100 Series (Xenogen Corp., Alameda, Calif., U.S.A.). A 2'-CH$_3$-MPTP-treated pair comprising of a transgenic and a non-transgenic neonatal mouse was positioned beside one another and held in position without anesthesia by physically restraining the mice on the lower back using tape. This was in view of a recent study which reported that ketamine, widely used in pediatric anaesthetic exhibits developmental neurotoxicity in neonatal rats by increasing the rate of neuronal apoptosis (Scallet et al., 2004). Subsequently, the pair of neonatal mice were fluorescently imaged with the GFP filter set equipped with the IVIS system. The image acquisition time was ten seconds. The same procedure was applied on the control pair injected with saline as well. Result of the neurotoxic effect of 2'-CH$_3$-MPTP on the mice was expressed as relative fluorescence (RF), a ratio between the total GFP fluorescent signals detected from the region of interest (ROI) in transgenic (Tg) mouse and the tissue autofluorescence signals from the ROI in non-transgenic (nTg) mouse (Tg$_{ROI}$/nTg$_{ROI}$). The area of the ROI for both mice is exactly the same and is identical throughout all the ROI used in the study to quantify the radiances. To minimize any variations due to the imaging system, three images were captured for each pair of treated and control mice and the mean value derived used as the quantitative reading for that particular pair. The values of the control (n=5 pairs of mice) and treated groups (n=5 pairs of mice) were expressed as means±SEM and statistical significance was evaluated using Student's two-tailed paired t-test.

Immunohistochemistry

In order to determine whether the photons were being emitted from the astrocytes in the CNS, the brains were harvested and fixed with 4% paraformaldehyde in 0.1 M phosphate buffer saline (PBS, pH 7.4) for 4 hr at 4° C. The brains were then washed three times in PBS with an incubation time of 15 min each time before soaking in 30% sucrose overnight at 4° C. All brains were embedded in freezing medium after immersing the tissues in liquid nitrogen prior to mounting and sectioning them using a cryostat (Leica Microsystems, Nussloch GmbH; CM-3050S). Coronal cryosections, 20 µm in thickness of the substantia nigra (bregma −3.16 mm, interaural 0.64 mm) were used for immunohistochemistry according to the Atlas of Mouse brain (Franklin and Paxinos, 2001). Each of the control and treated group contained 4 animals (n=3).

For tyrosine hydroxylase (TH) and GFAP immunostaining, a rabbit anti-TH polyclonal antibody (Chemicon International, Temecula, Calif., USA; Ab-152) and a rabbit anti-GFAP polyclonal antibody (DakoCytomation, Denmark; Z-0334) were used. The cryosections were washed for 5 min in 0.15 M 1×PBS followed by incubating for 4 hr at 4° C. in blocking solution of PBS containing 0.1% (v/v) Triton X-100 and 10% nonimmune goat serum. The cryosections were then washed in 0.15 M 1×PBS three times, each for 15 min. The brain sections were then incubated overnight with anti-TH antibody (1:200) and anti-GFAP antibody (1:200), in 1×PBS containing 0.01% (v/v) Triton X-100 and 1% nonimmune goat serum at 4° C. After a three times 15 min rinse in 1×PBS, the sections were incubated with Texas-red conjugated goat polyclonal to rabbit secondary IgG antibody (Abcam Ltd, Cambridge, U.K.; Ab-7088) at 1:100 dilution in PBS containing 0.01% (v/v) Triton X-100 and 1% nonimmune goat serum for 2 hr at room temperature. After another three times 15 min rinse in 1×PBS, the sections were coverslipped in 10 µl of the fluorescence medium and viewed under the confocal laser scanning microscope (Olympus Optical Co. Ltd. Tokyo, Japan; IX-71).

Results
Effect of 2'-$CH_3$-MPTP on GFP Fluorescence Level

Figure 1B:
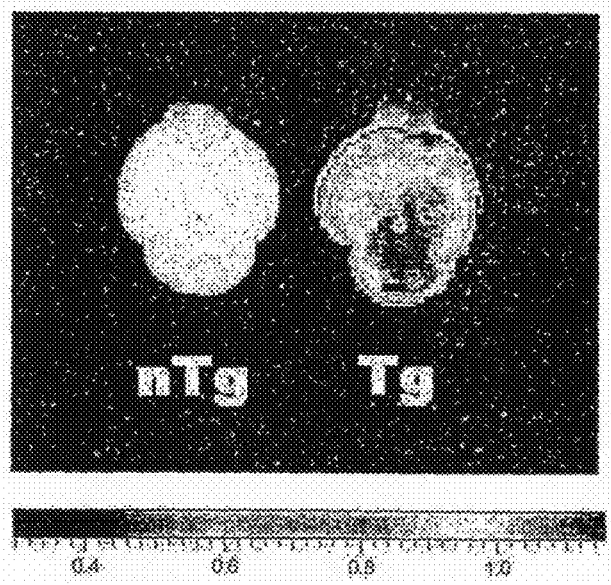

Innate GFP fluorescence was detected from the ROI in the brains of the mice and the radiances from the neural region was quantified in photons/sec/$cm^2$/steradian (sr) using the Living Image® software (Xenogen Corp.) as shown in FIG. 1A. In order to determine whether the photons were being emitted from the astrocytes in the CNS, the brains were removed and imaged ex vivo after the last in vivo imaging time point (FIG. 1B). Using this platform, a qualitative and quantitative comparison between the GFP fluorescence of a control and a treated transgenic mouse is made available.

Figure 2:
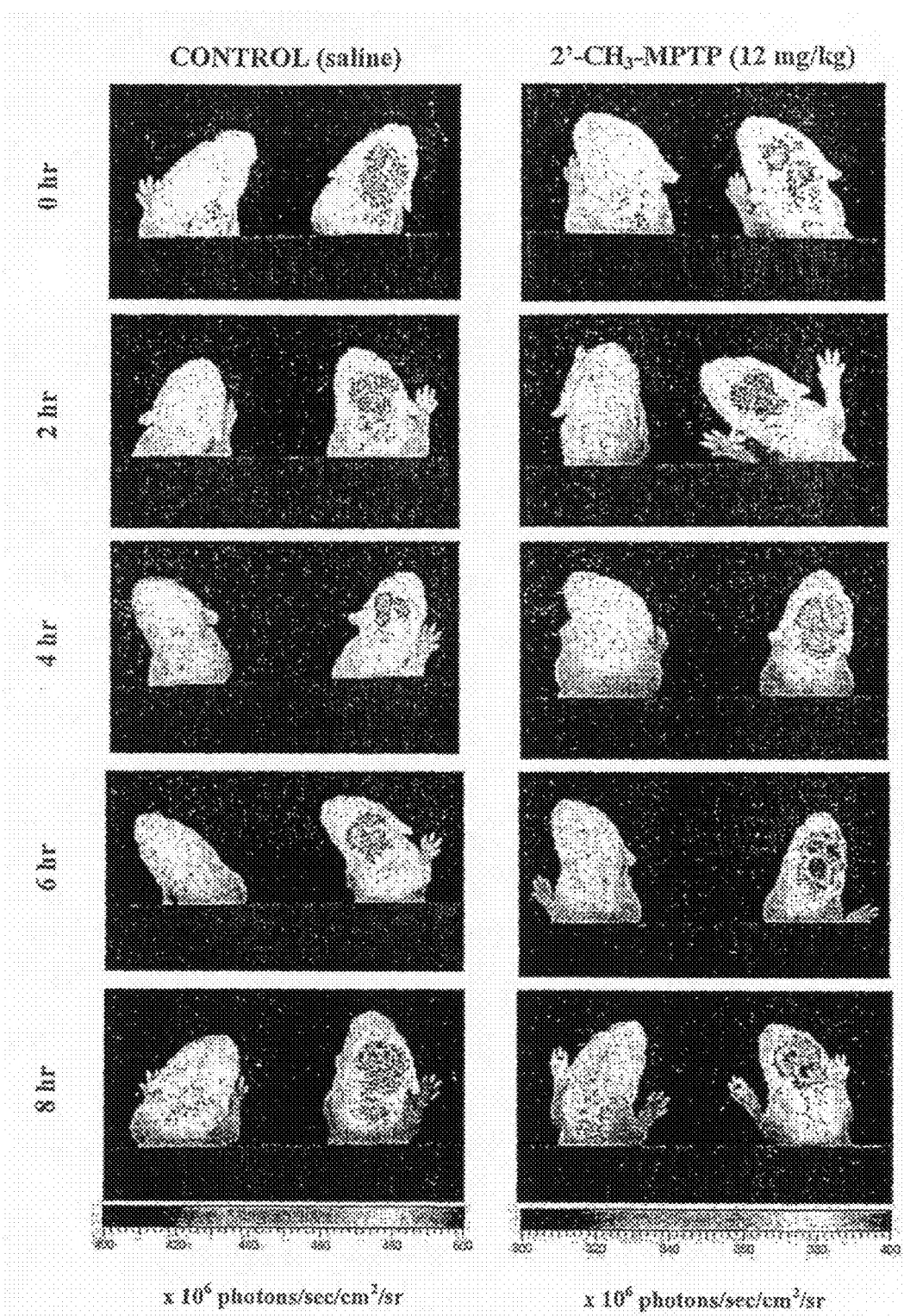
Figure 3:
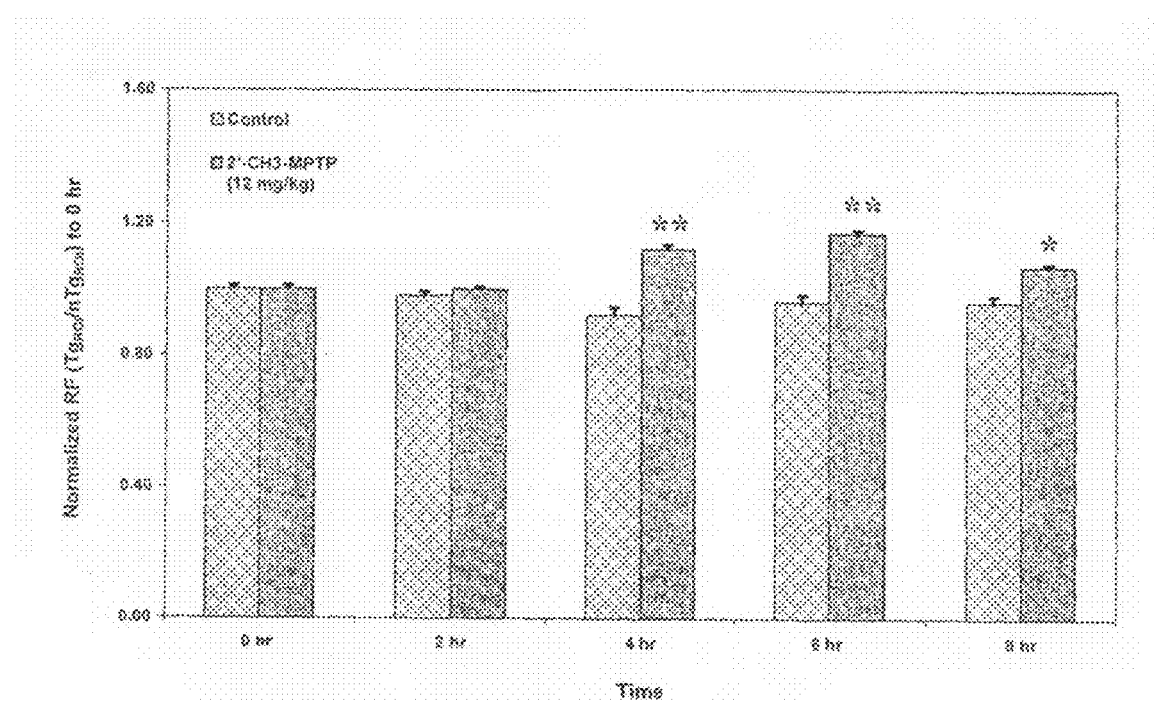

As illustrated in the in vivo images in FIG. 2, the transgenic neonatal mice that received a single dose of 2'-$CH_3$-MPTP (12 mg/kg sc) showed the most significant increase of GFP fluorescence (photons/sec/$cm^2$/sr) in the ROI over its non-transgenic counterpart as well as over the transgenic control mice at 6 hr post-treatment. The quantification in GFP fluorescence shown in FIG. 3 further strengthen the observation made in the previous figure that a significant difference in relative fluorescence (RF), between the 2'-$CH_3$-MPTP-treated and control group was recorded at 4 hr, 6 hr and 8 hr after treatment, with the treated group at 6 hr post-treatment showing the most significant increase of 22% mean over the control group ($P<0.01$). Similarly in the 2'-$CH_3$-MPTP group and comparing to 0 hr, a significant increase in RF occurred between 4 hr, 6 hr and 8 hr after treatment, with the most significant increase of 17% mean emerging at 6 hr after treatment ($P<0.0001$). No significant difference in RF occurred between the different time intervals within the control group (FIG. 3).

GFAP Immunohistochemistry

Figure 4:
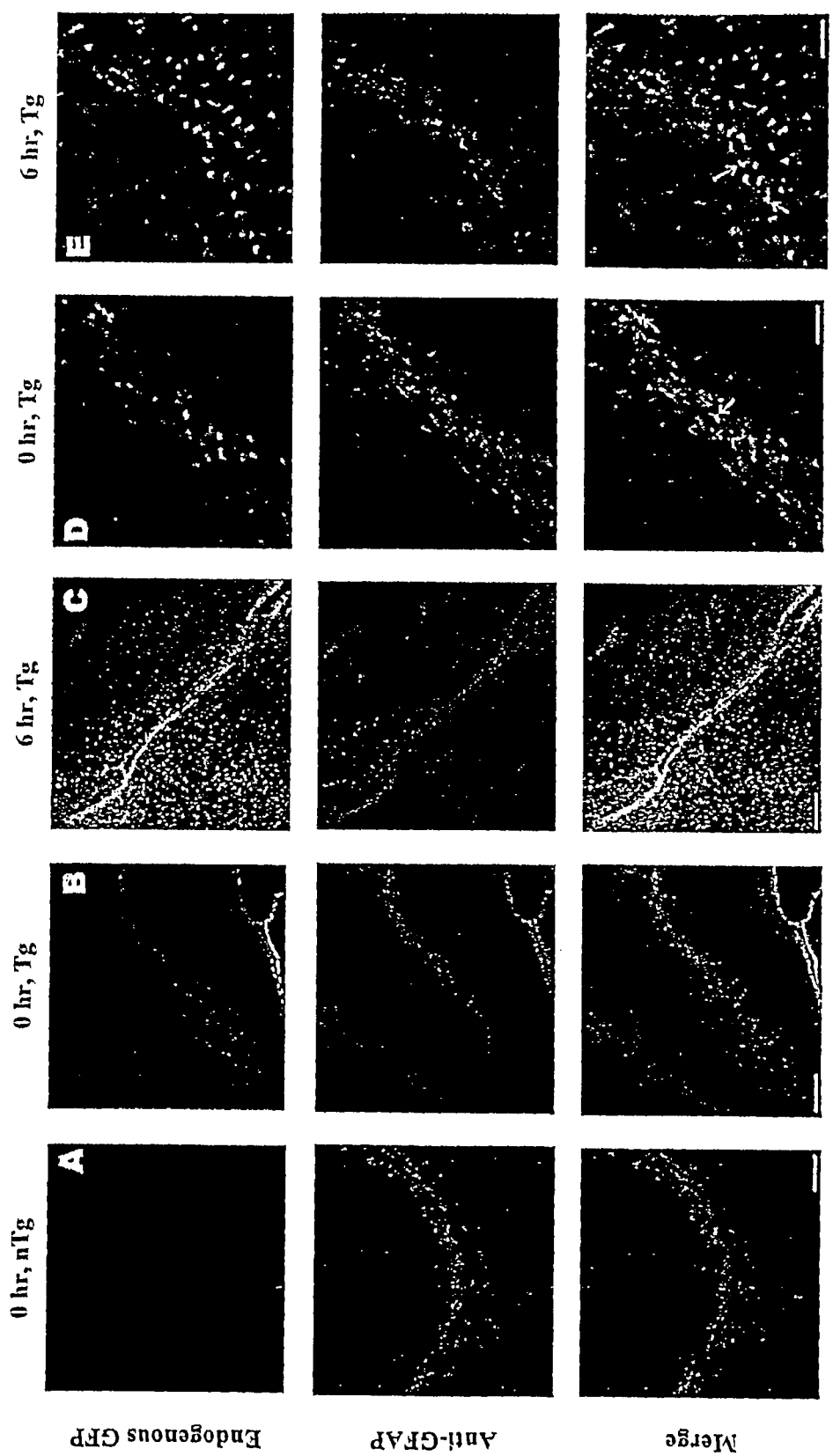

Representative images of GFAP immunostaining in the hippocampus are shown in FIG. 4. GFP expression in the astrocytes was evidently increased in the ventricle and hippocampus area 6 hr after one-time 2'-$CH_3$-MPTP (12 mg/kg sc) treatment. There was no existence of GFP expression in the non-transgenic mice (FIG. 4A). To verify that GFP-expressing cells were indeed astrocytes, we performed immunostaining on the same sections for GFAP and found that co-localization between the GFAP immuno-positive perivascular astrocytes at the hippocampal fissure and endogenous GFP-marked astrocytes occur predominantly in the processes and not the cell bodies (examples of dual-labeled cell processes are indicated by arrows in both FIGS. 4D and 4E).

TH Immunohistochemistry Staining

Figure 5:
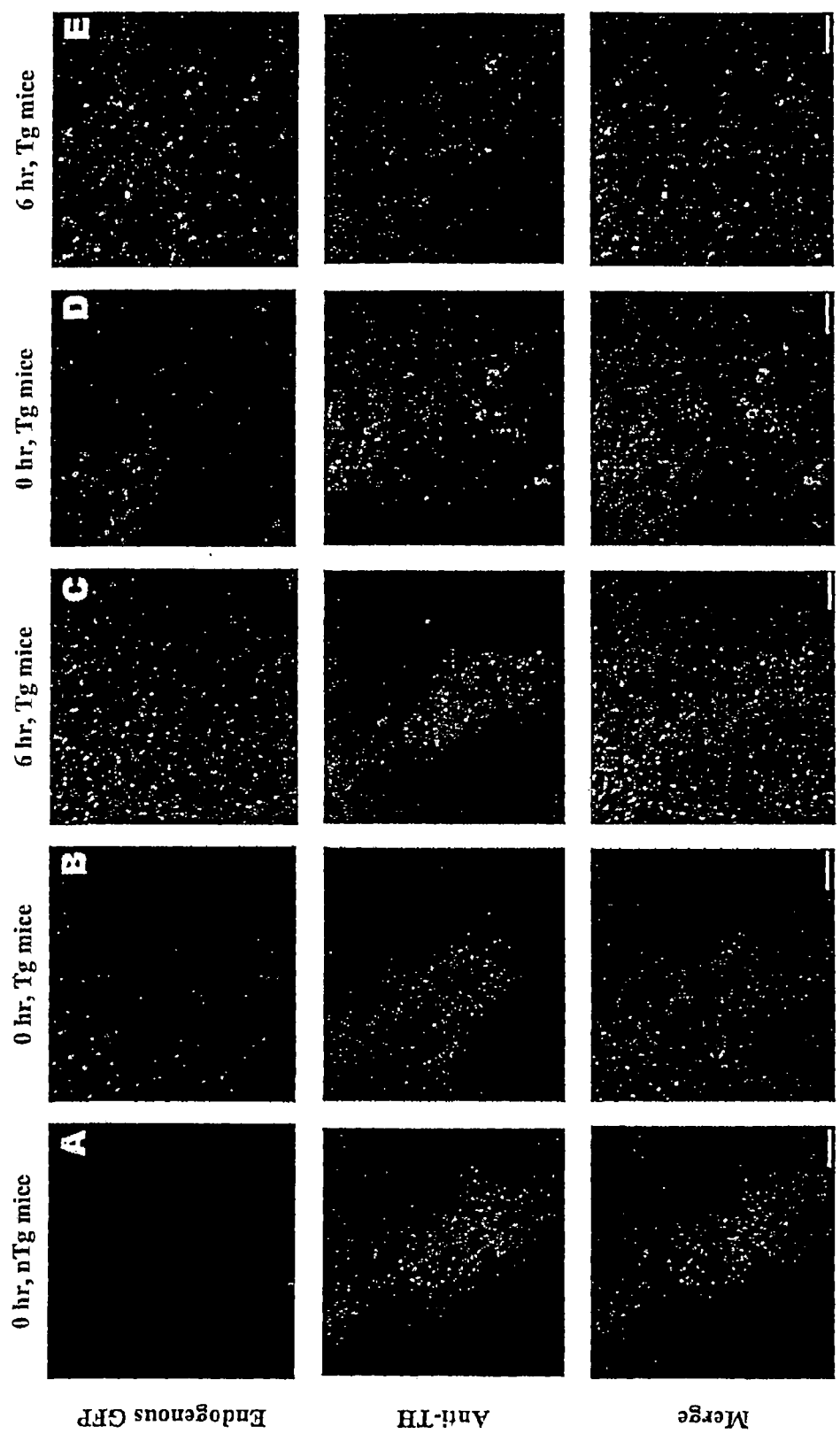

Representative images of TH immunostaining in the substantia nigra compact (SNC) are shown in FIG. 5. Dopaminergic neurons with the TH antibody are larger in size (~20 µm) compared to the non-IHC stained endogenous GFP-marked astrocytes (~10 µm) and were easily detectable in the SNC of the 2'-$CH_3$-MPTP-treated neonatal mice. The bodies or fibers of dopaminergic cells were intensely stained with evident immuno-positive processes in the SNC. No visual reduction in the TH immuno-positive fibers and cell bodies were observed 6 hr after 2'-$CH_3$-MPTP (12 mg/kg sc) treatment. However, up-regulation of expression of the GFAP-GFP transgene in the astrocytes could clearly be seen at 6 hr post-treatment as compared to 0 hr. As shown in FIG. 5A, the dopaminergic neurons in the SNC of non-transgenic mice were stained immuno-positive for TH but the glial cells produces no expression of the transgene. There was no co-localization between the TH immuno-positive dopaminergic neurons and the non-IHC stained endogenous GFP-marked astrocytes.

EXAMPLE 2

Imaging of Transgenic GFAP-GFP Adult Mice

Skin Flap in vivo Imaging

Skin flap, which is a tear of the skin away from the body which leaves one side of the skin still attached, was performed on the anesthetized transgenic GFAP-GFP adult mice. Using an IVIS Imaging System 100 Series (Xenogen Corp., Alameda, Calif., U.S.A.), in vivo imaging was conducted successfully on the skin flapped area of the brain and the liver. A low fluorescence black paper was used to shield the tissue autofluorescence from the rest of the mouse body, exposing only the skin flap region of the brain (FIG. 6A) and liver (FIG. 6B).

Ex vivo Imaging

As illustrated in the images in FIGS. 2A-2D, the brains, livers, kidneys and sciatic nerves of both transgenic (Tg) and non-transgenic (nTg) adult mice were removed and imaged ex vivo using the IVIS imaging system. A significant difference between the Tg and nTg mice could be observed from the pseudocolor images which correspond to its numerical value of the number of photons emitted. Presently, feasibility studies are being conducted for alternative imaging modalities for the adult mice.

EXAMPLE 3

Non-Invasive Brain Imaging Method for Studying Parkinsonism and Neurotoxicity in Neonatal Transgenic Mice Experimental Procedures
Animals The study was conducted on 4 day old neonatal mice (3-5 g body weight at the time of experiment). Animals had free access to food and water and efforts were made to minimize the number of animals used and their suffering.

Toxin Injection

The neurotoxin used was 2'-$CH_3$-MPTP. 4 injections of 8 mg/kg of MPTP were administered subcutaneously every 2 hours and the in vivo neural images obtained at 24 hrs, 48 hrs and 72 hrs after treatment.

BCA™ Protein Assay and Western Blot

For BCA™ protein assay and western blot, the mice were sacrificed 24 hours after treatment. The brain was removed and then lysed in sample buffer containing phosphate buffered saline (PBS) and proteinase inhibitor. Total protein is determined by the bicinchoninic acid (BCA) method using bovine serum albumin (BSA) as standard. Samples were then subjected to NuPAGE Bis-Tris electrophoresis using NUPAGE Novex Bis-Tris gel (4%-12%). Each sample contains 15 µg of protein. After electrophoresis, the proteins were transferred onto the nitrocellulose membrane. The membrane was blocked with 5% non-fat dried milk and 0.1% Tween 20 in PBS (PBS-T) at 4° C. overnight. The membrane was then incubated in a 1:1000 dilution of polyclonal rabbit anti-GFAP antibody (Dako)/rabbit polyclonal to GFP antibody (abcam) for 1 hour at room temperature and then washed and incubated with PBS-T for 3×15 minutes. The incubation and washing process of 5 minutes was repeated 3 times after incubating for 1 hour at room temperature with secondary goat anti-rabbit IgG-HRP antibody (Santa Cruz) at 1:2000 dilution. The secondary antibodies were visualized by using chemiluminescent detection reagents (ECL Plus, Amersham) and autoradiography film. After western blot is carried out, the nitrocellulose membranes are brought to be imaged under the IVIS machine. When using ECL Plus detection reagents, combined HRP and peroxide catalyzed oxidation of the Lumigen PS-3 Acridan substrate generates thousands of acridinium ester intermediates per minute. These intermediates react with peroxide under slight alkaline conditions to produce a sustained, high intensity chemiluminescence with maximum emission at 430 nm. This chemiluminescent signal can be picked up using the IVIS imaging system. An image of the membrane with colours depicting the luminescent intensity is obtained.

Real-time RT-PCR

For real-time RT-PCR, the mice were sacrificed 24 hours after treatment. The brain was removed and then lysed in buffer RA1 and β-mercaptoethanol. Total RNA from the brain was isolated using NucleoSpin® RNA II kit. Total RNA was reverse-transcribed with random hexamers and real-time RT-PCR was performed on the cDNA to quantify gene expression.

Experimental Results

MPTP (4×8 mg/kg)

In vivo Neural Images

Figure 8:
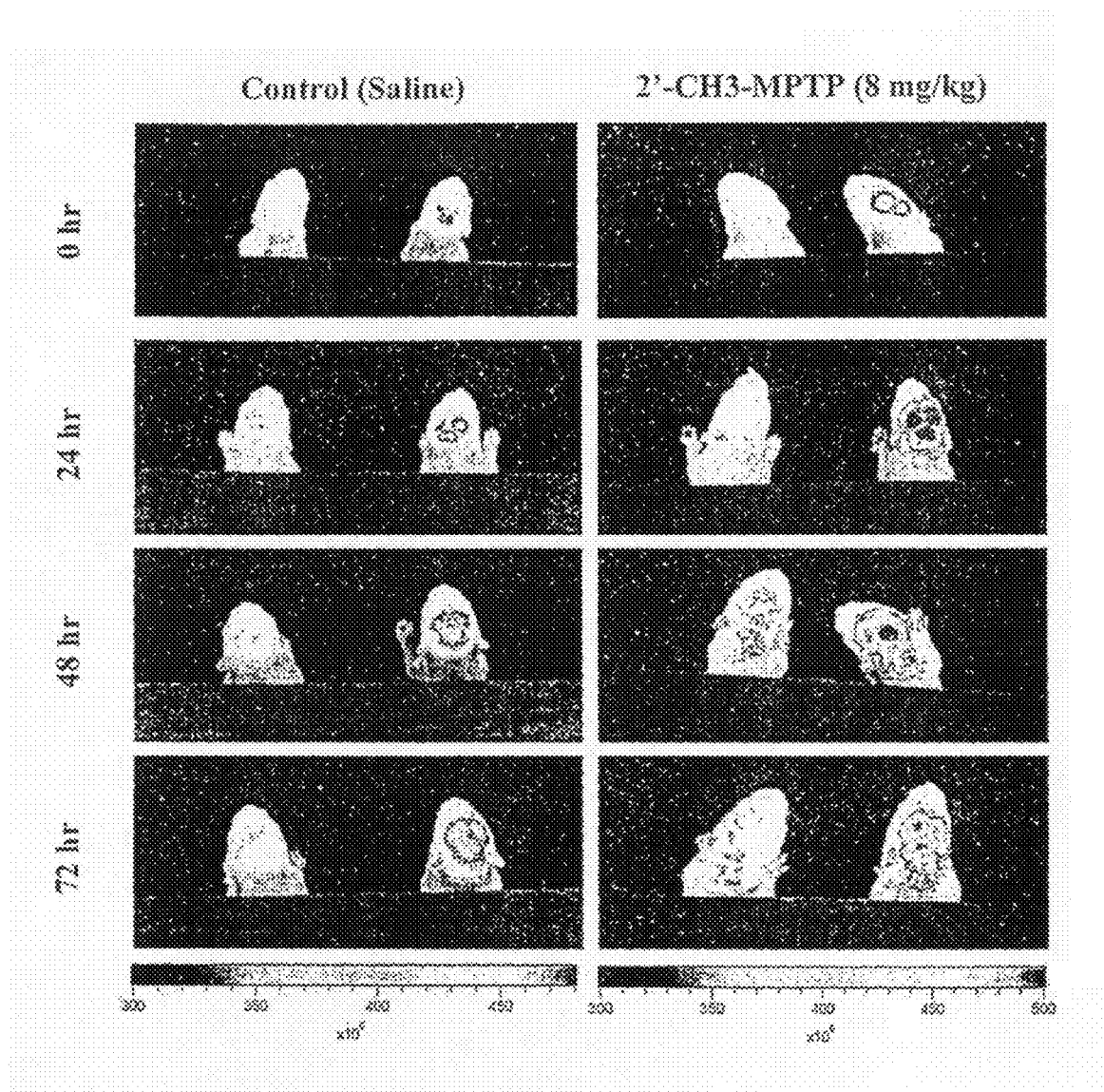
Figure 9:
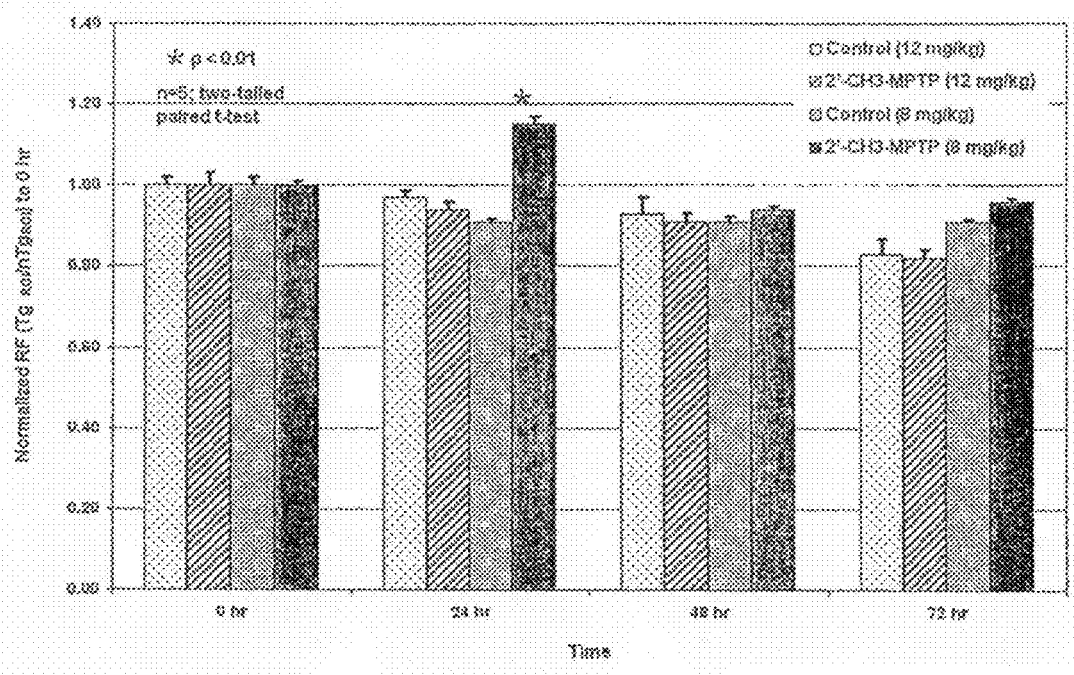

As shown in FIG. 8, innate GFP fluorescence was detected from the region of interest (ROI) in the brains of the mice and the radiances from the neural region was quantified in photons/sec/$cm^2$/steradian (sr) using the Living Image® software (Xenogen Corp.). As illustrated in the in vivo images, the transgenic neonatal mice that received 4 doses of MPTP (8 mg/kg sc) showed the most significant increase of GFP fluorescence (photons/sec/$cm^2$/sr) in the ROI over the control mice at 24 hours post-treatment. The quantification in GFP fluorescence shown in FIG. 9 shows that a significant difference in relative fluorescence (RF), between the MPTP-treated and control group was recorded at 24 hours after treatment, showing a statistically significant increase of 15% mean over the control group ($p<0.01$). With the transgenic neonatal mice that received a single dose of MPTP (12 mg/kg sc) as well as within the control group, no significant difference in RF occurred between the different time intervals (FIG. 9).

Western Blot Results

Figure 10A:
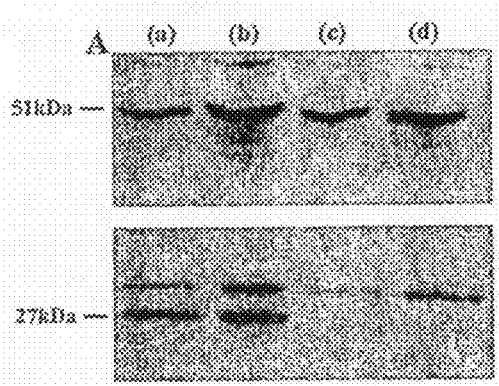
Figure 10B:
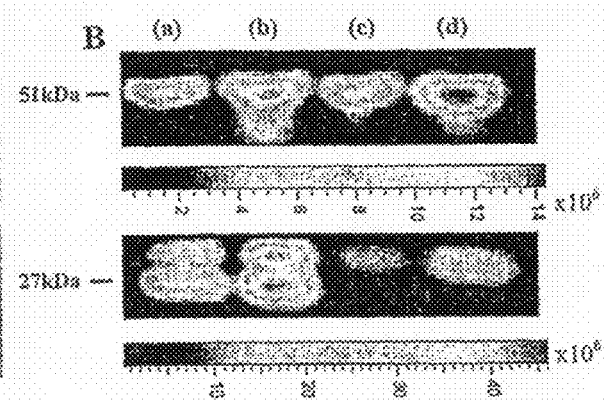

From the western blot results shown in FIG. 10A, bands were detected at approximately 51 kDa which corresponds to the reported molecular size of mouse GFAP using the Dako anti-rabbit GFAP antibody. Bands were also detected at approximately 27 kDa which corresponds to the reported molecular size of mouse GFP using the Abcam anti-rabbit GFP antibody. From the thickness of the bands, it can be seen that the amount of GFAP and GFP proteins increased from 0 to 24 hours in transgenic mice (comparing lane a and b). The amount of GFAP proteins also increased from 0 to 24 hours in the non-transgenic mice (comparing lane c and d in GFAP western blot). No GFP proteins were detected in the non-transgenic mice (lane c and d in GFP western blot) because of the absence of the transgene. When the western blot membranes were imaged using IVIS, the coloured depiction of amount of proteins present gave the same results (refer to FIG. 10B). This reinforces the fact that GFAP is upregulated following the administration of MPTP, which in turn leads to the upregulation of GFP as well.

Real-time RT-PCR Results

Figure 11A:
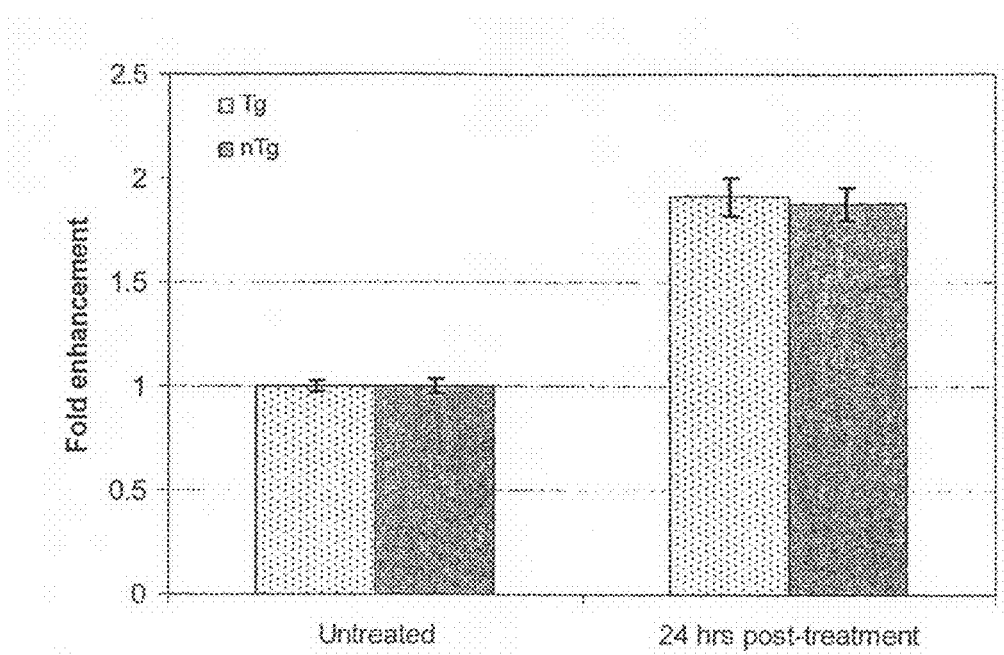
Figure 11B:
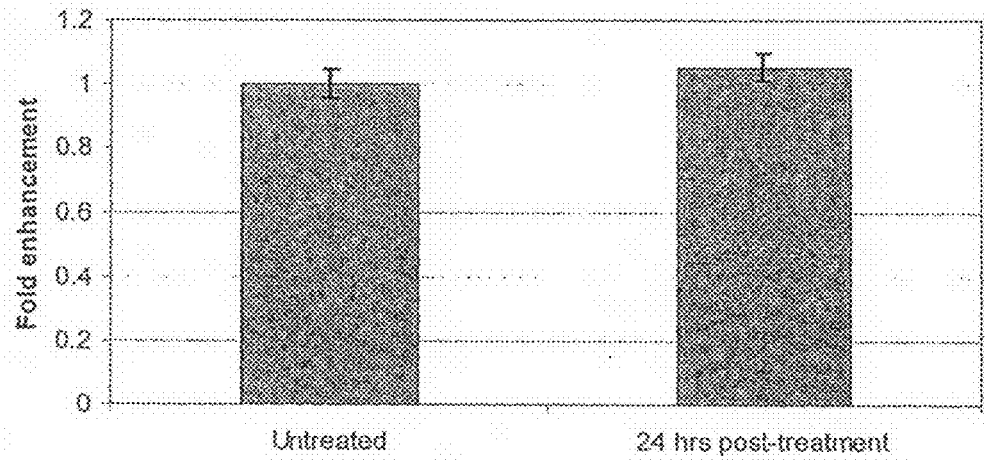

The study of the mRNA concurs with the results of the study of proteins in BCA and western blot and for a longer study period, the in vivo neural images as well. As shown in FIG. 11A, enhancement in gene expression of GFAP at 24 hours after MPTP treatment for both the transgenic and non-transgenic mouse was found to be statistically significant at about 91% ($p<0.01$) and 88% ($p<0.01$) respectively as compared to the untreated mice. However, gene expression of GFP at 24 hours after MPTP treatment was found to have no statistically significant enhancement as compared to the untreated mice (FIG. 11B). This explains the decrease in the relative fluorescence of the neural images at 48 hours and 72 hours after MPTP treatment (refer to FIGS. 8 and 9).

Endogenous GFP and TH Immunohistochemistry

Figure 12:
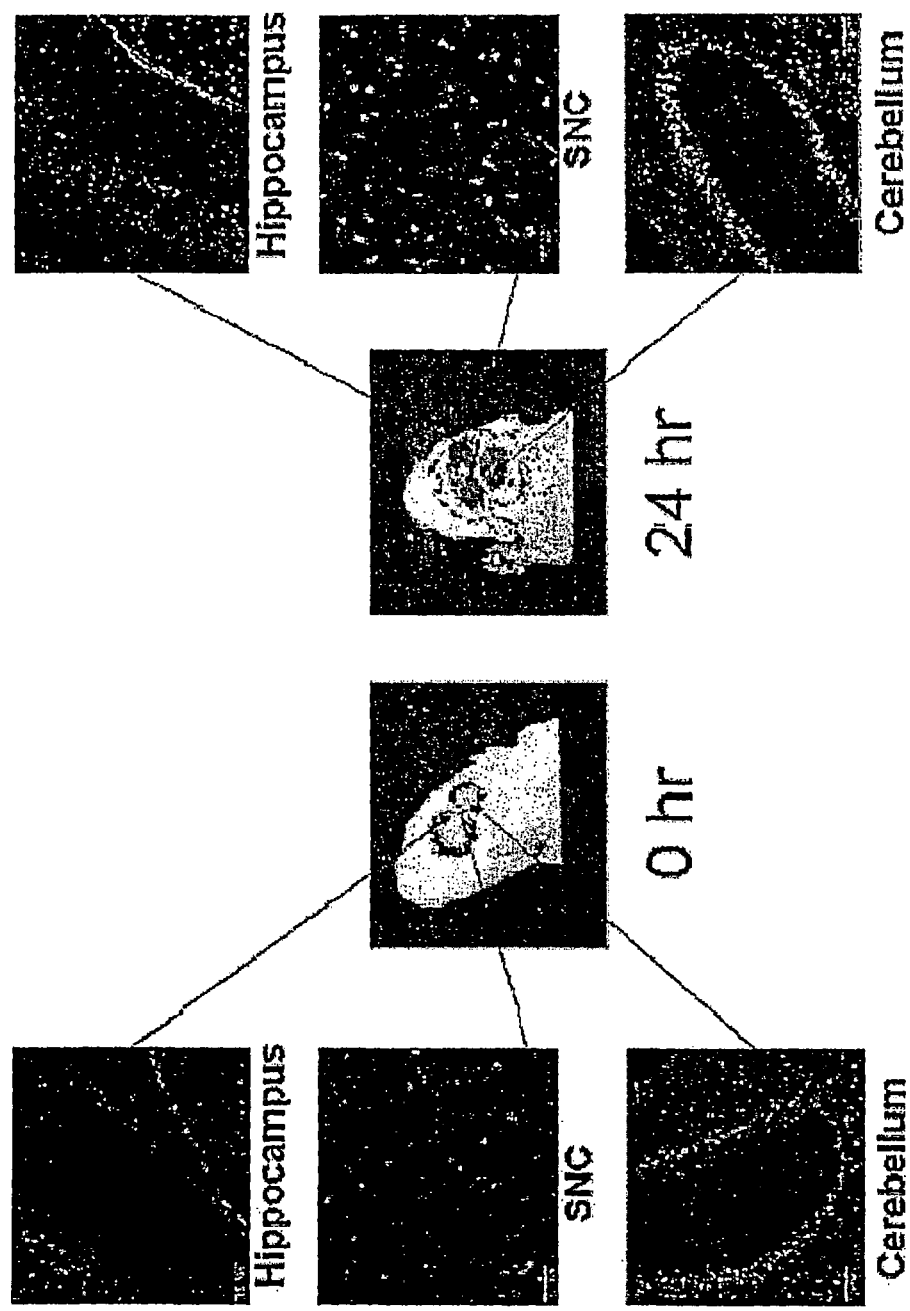
Figure 13:
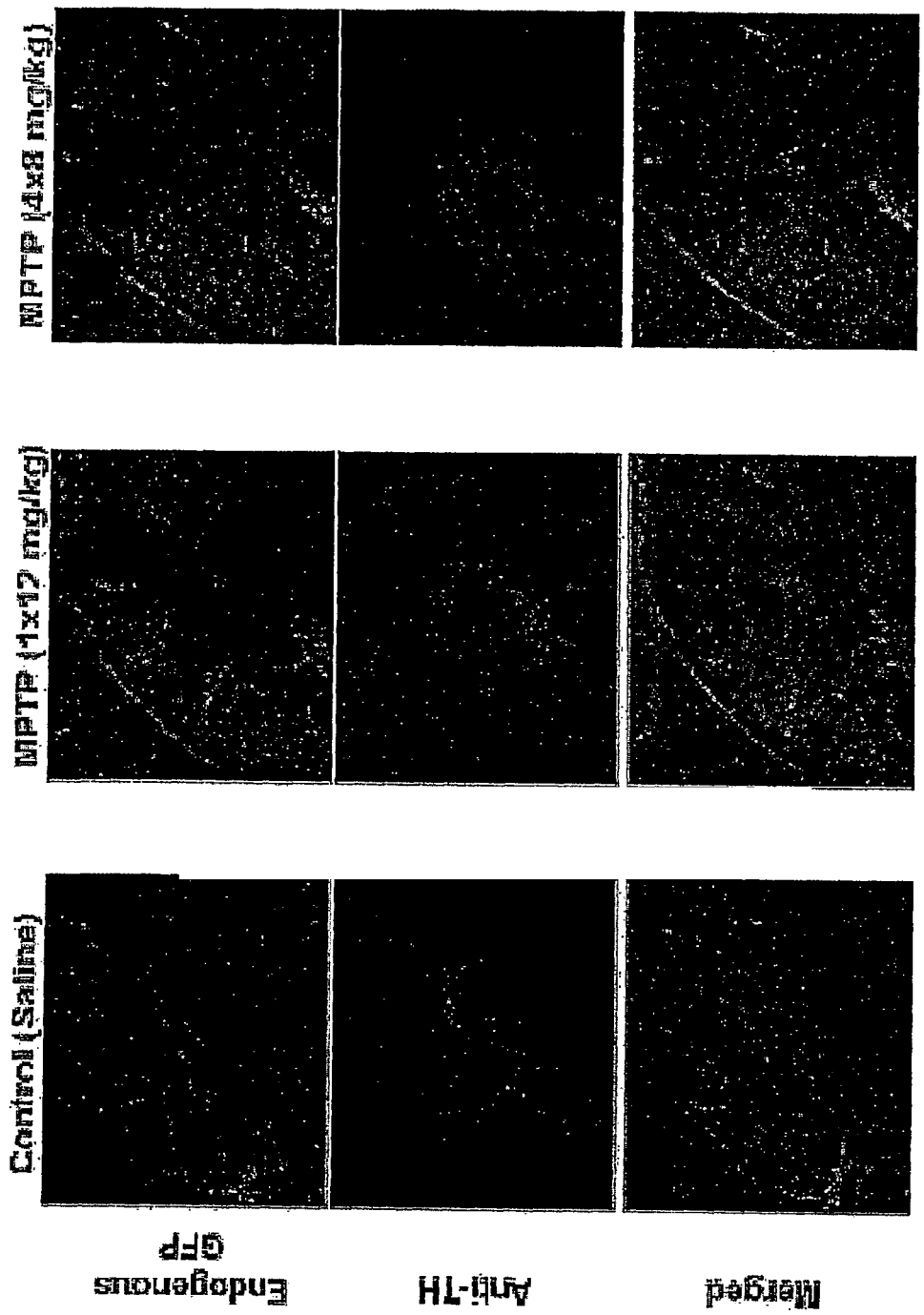

Results are shown in FIGS. 12 and 13.

EXAMPLE 4

Non-Invasive Brain Imaging Method for Studying Parkinsonism and Neurotoxicity in Neonatal Transgenic Mice Experimental Procedures Animals The study was conducted on 4 days old neonatal mice (3-5 g body weight at the time of experiment). Animals had free access to food and water and efforts were made to minimize the number of animals used and their suffering.

Toxin Injection

The neurotoxins used were 2'-$CH_3$-MPTP and Kainic Acid (KA). MPTP was administered in dosages 12 mg/kg with one injection. KA was used in dosages 2 mg/kg with one injection. All injections were carried out subcutaneously.

BCA™ Protein Assay and Western Blot

For mice treated with MPTP (1×12 mg/kg), they were sacrificed 6 hours after treatment. The brain was removed and then lysed in sample buffer containing phosphate buffered saline (PBS) and proteinase inhibitor. Total-protein is determined by the bicinchoninic acid (BCA) method using bovine serum albumin (BSA) as standard. Samples were then subjected to NuPAGE Bis-Tris electrophoresis using NuPAGE Novex Bis-Tris gel (4%-12%). Each sample contains 15 µg of protein. After electrophoresis, the proteins were transferred onto the nitrocellulose membrane. The membrane was blocked with 5% non-fat dried milk and 0.1% Tween 20 in PBS (PBS-T) at 4° C. overnight. The membrane was then incubated in a 1:1000 dilution of polyclonal rabbit anti-GFAP antibody (Dako)/rabbit polyclonal to GFP antibody (abcam) for 1 hour at room temperature and then washed and incubated with PBS-T for 3×15 minutes. The incubation and washing process of 5 minutes was repeated 3 times after incubating for 1 hour at room temperature with secondary goat anti-rabbit IgG-HRP antibody (Santa Cruz) at 1:2000 dilution. The secondary antibodies were visualized by using chemiluminescent detection reagents (ECL Plus, Amersham) and autoradiography film. The same procedure is carried out for mice treated with KA (1×2 mg/kg). After western blot is carried out, the nitrocellulose membranes are brought to be imaged under the IVIS machine. When using ECL Plus detection reagents, combined HRP and peroxide catalyzed oxidation of the Lumigen PS-3 Acridan substrate generates thousands of acridinium ester intermediates per minute. These intermediates react with peroxide under slight alkaline conditions to produce a sustained, high intensity chemiluminescence with maximum emission at 430 nm. This chemiluminescent signal can be picked up using the IVIS imaging system. An image of the membrane with colours depicting the luminescent intensity is obtained.

Real-time RT-PCR

For mice treated with MPTP (1×12 mg/kg), they were sacrificed 2 hours after treatment. The brain was removed and then lysed in buffer RA1 and β-mercaptoethanol. Total RNA from the brain was isolated using NucleoSpin® RNA II kit. Total RNA was reverse-transcribed with random hexamers and real-time RT-PCR was performed on the cDNA to quantify gene expression. The same procedure is carried out for mice treated with KA (1×2 mg/kg).

Experimental Results

MPTP (1×12 mg/kg)

Western Blot Results

Figure 14:
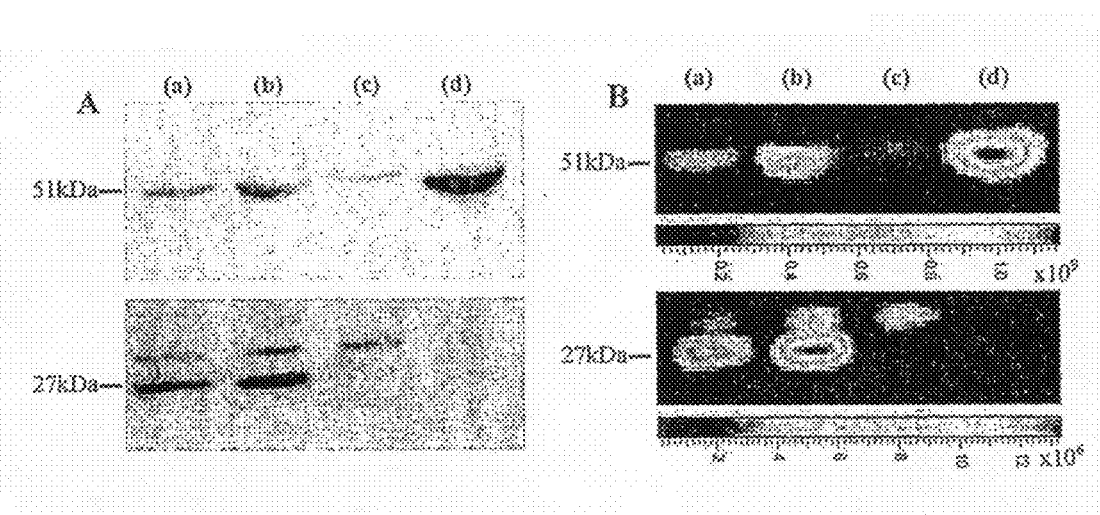

From the western blot results shown in FIG. 14A, bands were detected at approximately 51 kDa which corresponds to the reported molecular size of mouse GFAP using the Dako anti-rabbit GFAP antibody. Bands were also detected at approximately 27 kDa which corresponds to the reported molecular size of mouse GFP using the Abcam anti-rabbit GFP antibody. From the thickness of the bands, it can be seen that the amount of GFAP and GFP proteins increased from 0 to 6 hours in transgenic mice (comparing lane a and b). The amount of GFAP proteins also increased from 0 to 6 hours in the non-transgenic mice (comparing lane c and d in GFAP western blot). No GFP proteins were detected in the non-transgenic mice (lane c and d in GFP western blot) because of the absence of the transgene. When the western blot membranes were imaged using IVIS, the coloured depiction of amount of proteins present gave the same results (refer to FIG. 14B). This reinforces the fact that GFAP is upregulated following the injection of MPTP, which in turn leads to the upregulation of GFP as well.

Real-time RT-PCR Results

Figure 15:
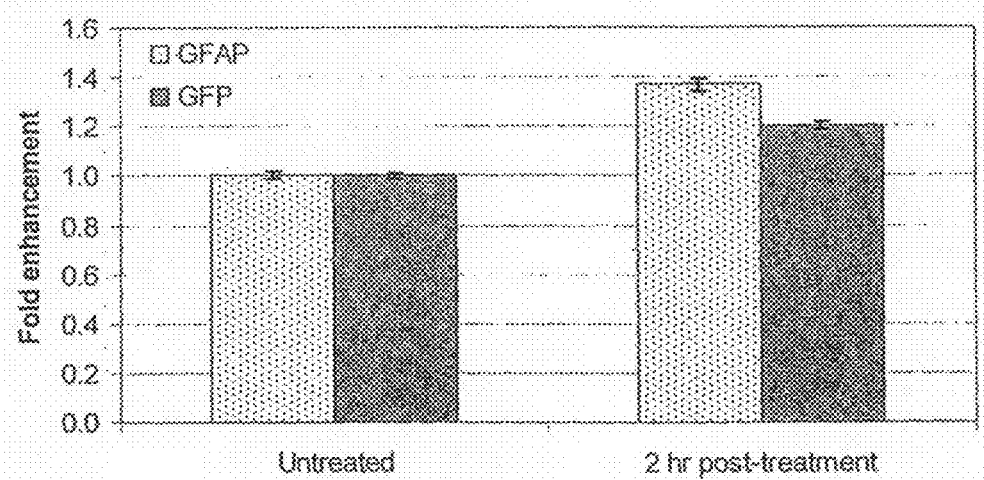

The study of the mRNA concurs with the results of the study of proteins in BCA and western blot. As the upregulation of GFAP and GFP proteins peaked at 6 hours, upregulation of GFAP and GFP mRNAs were found to occur as early as 2 hours after MPTP treatment. The difference in time accounts for the time needed for the mRNAs to be translated into proteins. As shown in FIG. 15, the enhancement in gene expression at 2 hours after MPTP treatment for both the GFAP and GFP was found to be statistically significant at about 47% ($p<0.001$) and 20% ($p<0.01$) respectively.

KA (1×2 mg/kg)

In vivo Neural Images

Figure 16:
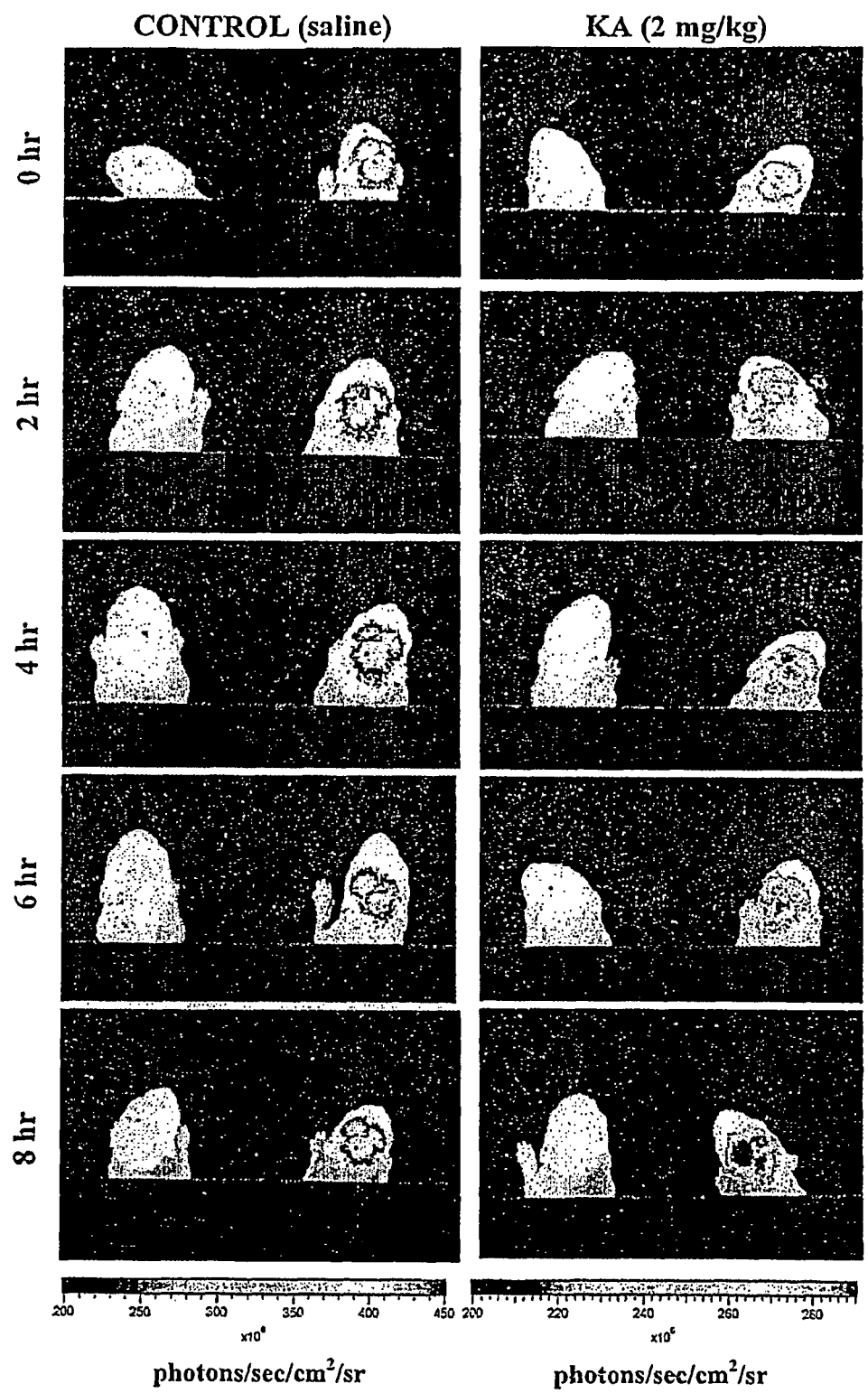
Figure 17:
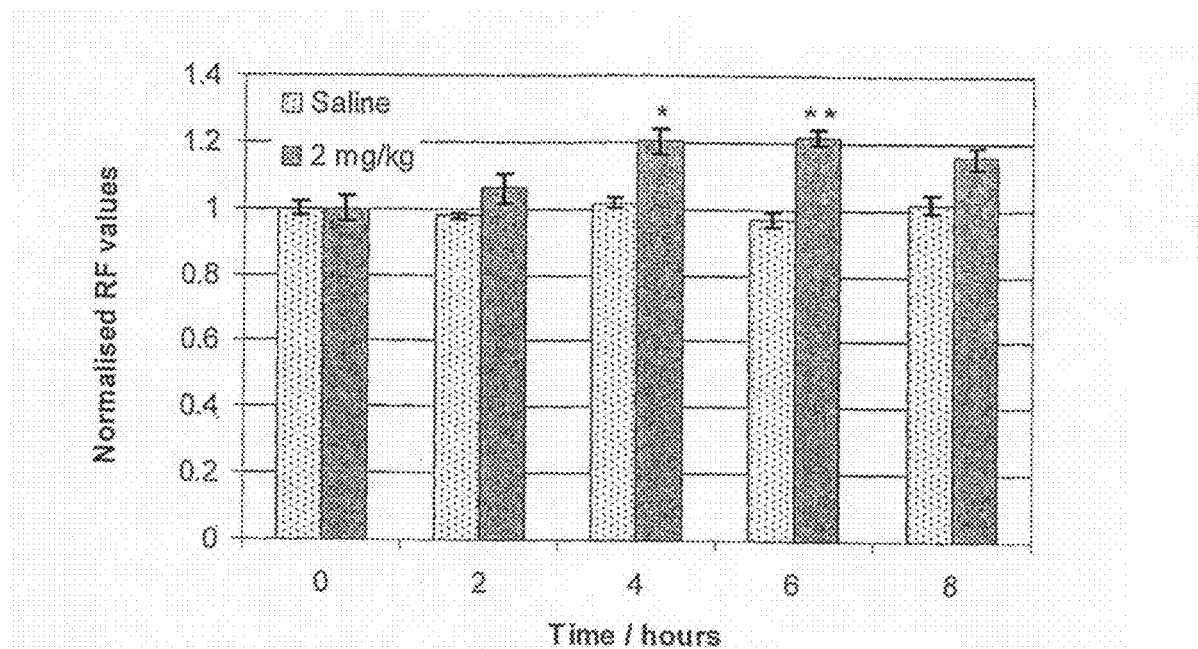

As shown in FIG. 16, innate GFP fluorescence was detected from the ROI in the brains of the mice and the radiances from the neural region was quantified in photons/sec/cm$^2$/steradian (sr) using the Living Image® software (Xenogen Corp.). As illustrated in the in vivo images, the transgenic neonatal mice that received a single dose of KA (2 mg/kg sc) showed the most significant increase of GFP fluorescence (photons/sec/cm$^2$/sr) in the ROI over its non-transgenic counterpart as well as over the transgenic control mice at 6 hr post-treatment. The quantification in GFP fluorescence shown in FIG. 17 shows that a significant difference in relative fluorescence (RF), between the KA-treated and control group was recorded at 4 hr and 6 hr after treatment, with the treated group at 6 hr post-treatment showing the most significant increase of 25% mean over the control group ($P<0.01$). Similarly in the KA group and comparing to 0 hr, a significant increase in RF occurred at 6 hr after treatment, with the most significant increase of 22% mean emerging at 6 hr after treatment ($P<0.05$). No significant difference in RF occurred between the different time intervals within the control group (FIG. 17).

Western Blot Results

Figure 18:
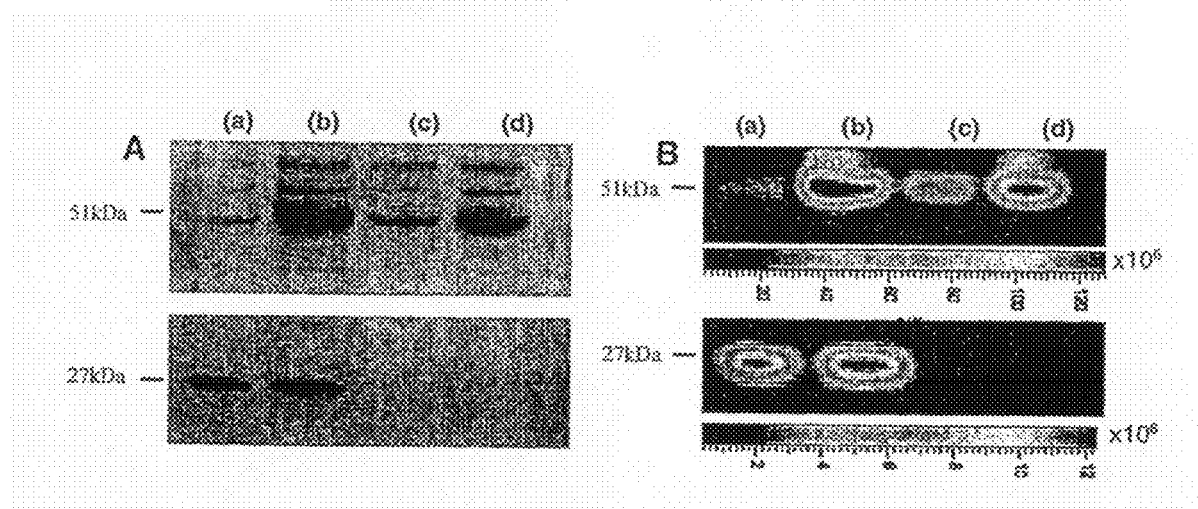

From the western blot results shown in FIG. 18A, bands were detected at approximately 51 kDa which corresponds to the reported molecular size of mouse GFAP using the Dako anti-rabbit GFAP antibody. Bands were also detected at approximately 27 kDa which corresponds to the reported molecular size of mouse GFP using the Abcam anti-rabbit GFP antibody. From the thickness of the bands, it can be seen that the amount of GFAP and GFP proteins increased from 0 to 6 hours in transgenic mice (comparing lane a and b). The amount of GFAP proteins also increased from 0 to 6 hours in the non-transgenic mice (comparing lane c and d in GFAP western blot). No GFP proteins were detected in the non-transgenic mice (lane c and d in GFP western blot) because of the absence of the transgene. When the western blot membranes were imaged using IVIS, the coloured depiction of amount of proteins present gave the same results (refer to FIG. 18B). This reinforces the fact that GFAP is upregulated following the injection of KA, which in turn leads to the upregulation of GFP as well.

Real-time RT-PCR Results

Figure 19:
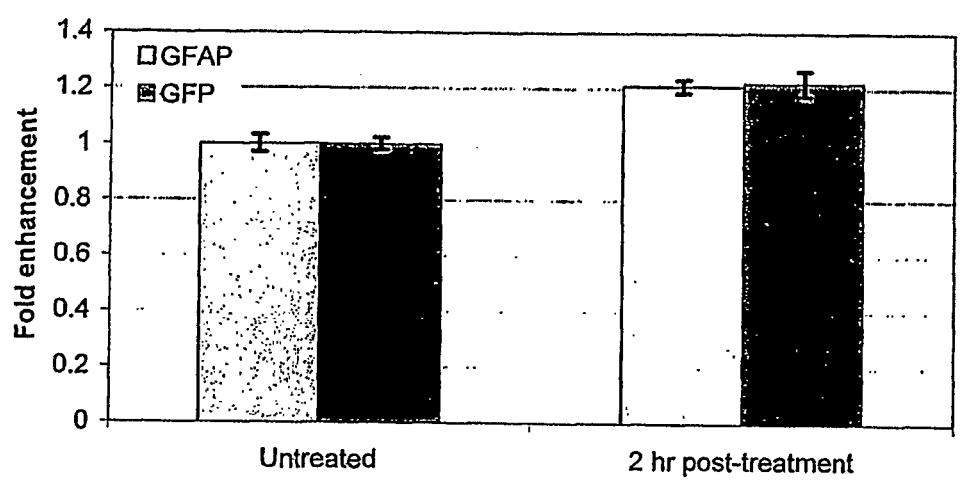
Figure 20:
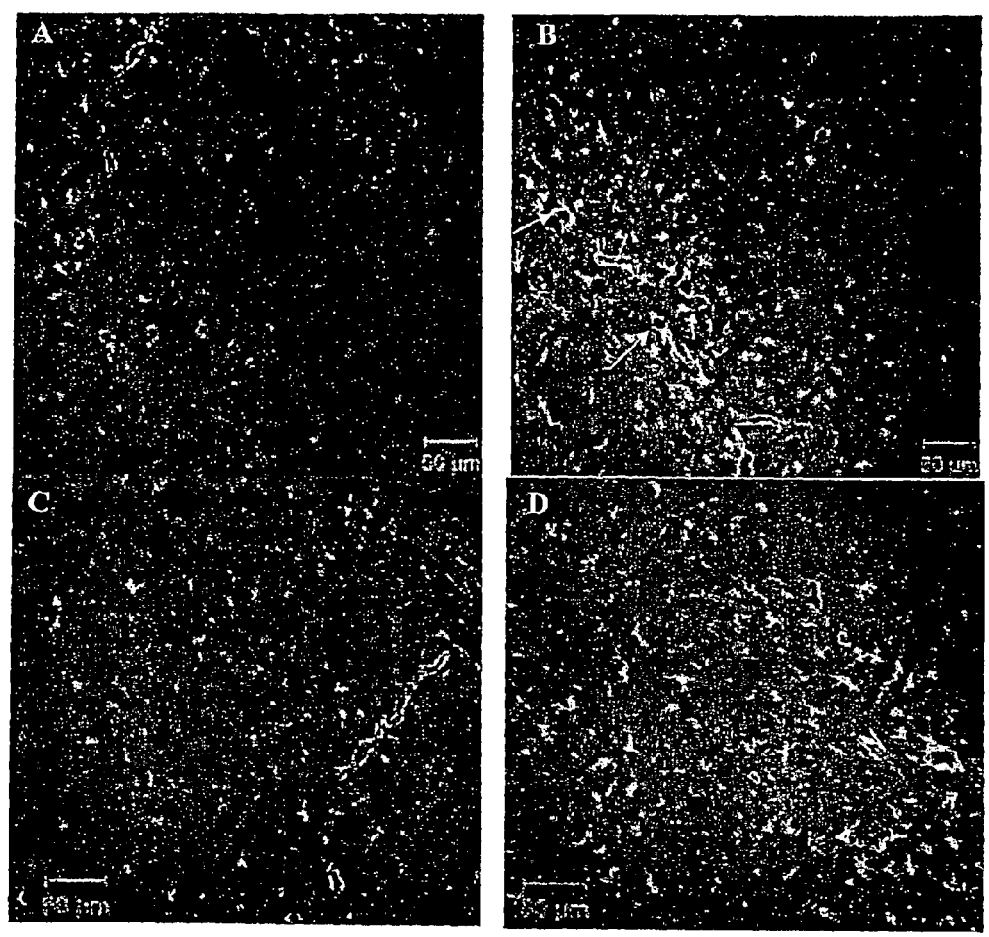

The study of the mRNA concurs with the results of the study of proteins in BCA and western blot. As the upregulation of GFAP and GFP proteins peaked at 6 hours, upregulation of GFAP and GFP mRNAs were found to occur as early as 2 hours after KA treatment. The difference in time accounts for the time needed for the mRNAs to be translated into proteins. As shown in FIG. 19, the enhancement in gene expression at 2 hours after KA treatment for both the GFAP and GFP was found to be statistically significant at about 21% ($p<0.01$) and 22% ($p<0.05$) respectively.

GFAP Immunohistochemistry

Representative images of GFAP immunostaining in the CA1, CA2 and CA3 sub-areas of the hippocampus were shown in FIG. 20A-D. GFP expression in the astrocytes was evidently increased in the various areas of the hippocampus 6 hr after one-time KA (2 mg/kg sc) treatment. To verify that GFP-expressing cells were indeed astrocytes, we performed immunostaining on the same sections for GFAP and found that co-localization between the GFAP immunopositive astrocytes at the hippocampal CA1 area and endogenous GFP-marked astrocytes occur predominantly in the processes and not the cell bodies (examples of dual-labeled cell processes are indicated by arrows in FIG. 20B).

Discussion of Examples

In the transgenic mouse model, the glial fibrillary acidic protein (GFAP) promoter drives the expression of green fluorescent protein (GFP). GFAP is an intermediate filament protein expressed predominantly in the astrocytes of the central nervous system (CNS). Changes in these glial cells can be used to monitor neuronal activity. Injury to the neurons in the CNS is a powerful inducer of GFAP. However, monitoring GFAP by in vitro assays necessitate sacrificing the animal. We have shown that non-invasive in vivo neural imaging of GFAP-GFP expression allows GFAP to be monitored over a period of time and reduces the number of animals sacrificed in the process.

$2'$-$CH_3$-MPTP is a neurotoxin that causes degeneration of dopaminergic neurons in the substantia nigra compacta. Kainic acid is a neurotoxin that causes excitotoxic brain insults. Both neurotoxins are known to elevate the GFAP expression. This can be developed into a model of non-invasive in vivo-imaging for the diagnosis and screening of treatments, i.e. candidate drugs and therapies; and the study of developmental neurotoxicity. Neonatal mice are injected with these neurotoxins and subsequent increases in the fluorescence of the GFAP-GFP transgene in the neonatal brains due to the effects of the neurotoxins were studied using the IVIS imaging system. In order to support the conclusion that the non-invasive in vivo neural imaging model is reliable in studying neural developments, in vitro assays were also carried out. BCA™ protein assay (GFP) and western blot were carried out to quantify the protein expression while real-time RT-PCR was used to quantify gene expression. These assays can be used to trace the changes taking place in the neonatal mice due to the administration of neurotoxins and the results can be compared with that of in vivo neural imaging.

For the past half-century, cell biology and molecular biology have been carried out on cells grown in dishes and by the extracellular analysis of cellular components including genes and proteins. The use of optical probes for tracking and reporting functional information on molecules, proteins and cells in vivo is a new and rapidly expanding technology. This technology has a large range of applications, including study of infectious disease, oncology, pharmacokinetics, pharmacodynamics, toxicology, and gene expression in bioluminescent or fluorescent reporters in transgenic animals (Contag et al., 2000, Rehemtulla et al., 2000, Yang et al., 2000, Zhang et al., 2001, Bhaumik and Gambhir, 2002, Bouvet et al., 2002, Ntziachristos et al., 2002). As illustrated by Hoffman (Hoffman, 2004), the advent of GFP as reporter gene is enabling a paradigm change in cell and molecular biology. Incorporating imaging technologies that are rapid and accessible into preclinical studies will yield more and higher-quality experimental data per protocol by increasing the number of times that quantitative data can be collected. By imaging the whole intact live animal at multiple time points, researchers can analyze biomolecular processes in presence of contextual influences of intact organs. It is an added benefit that with these methods fewer animals can deliver data with greater statistical significance and lower stress. Non-invasive methods can be used to create more predictive animal models that share the characteristics of longitudinal-study design, internal experimental control, molecular information, and quantitative data, and these methods will benefit both scientific inquiry and humane animal use. In addition, imaging can further improve these studies by guiding appropriate end-point-tissue sampling for histology or biochemical analysis.

One problem faced in this present study lies in the sources of autofluorescence. Typically, tissue autofluorescence caused by the endogenous chromophores in animal tissues including elastin, collagen, tryptophan, nicotinamide adenine dinucleotide (NADH), porphyrins and flavins is much higher than instrumental autofluorescence, particularly in the visible wavelength range (Troy et al., 2004). For in vivo imaging, tissue autofluorescence is a primary concern as it affects the ability to detect fluorescent probes of interest. As observed in this study, the autofluorescences from the neonatal mice increased as the mice develop from birth to adulthood. As a result, the inventors devised a safe-guard system to monitor the signal to noise (s/n) ratio by normalizing the total GFP fluorescence from the transgenic mouse with the autofluorescence from the non-transgenic mouse to produce a relative fluorescence (RF). If the RF breaches below a threshold value of 1.3 or 30% of the GFP signal detected from the transgenic mouse, then that particular data will be deemed as having too low a s/n ratio and thus too unreliable to be used to generate precise quantitative result.

Using $2'$-$CH_3$-MPTP as a model compound, the data obtained by the non-invasive in vivo neural imaging model were consistent with the presence of up-regulated astrocytes determined histologically. It is well documented that MPTP can specifically induce the neurodegenerative death of mesencephalic dopamine neurons in vivo and resulted in Parkinsonism of animals or Parkinson' disease of humans (Damier et al., 1999, German et al., 1999, Olanow and Tatton, 1999). Previous evidence suggested the potential role of astrocytes in the pathological processes of MPTP-induced Parkinsonism. For example, adult mice systematically injected with MPTP showed significant GFAP elevation in astrocytes and concurrently dopamine decrease in dopaminergic neurons in the striatum area of the brain (Reinhard et al., 1988, Chen et al., 2002, Dervan et al., 2004, Kurosaki et al., 2004). It is worth noting that a higher susceptibility to MPTP lesion in the brain was seen in older mice of the same genetic background (Ali et al., 1993). Compared to studies on MPTP action in adult mouse brain, there is a limited amount of literatures on how astrocytes in neonatal brain react to MPTP, presumably due to lack of appropriate methodology which permits the repeated non-invasive measurements of GFAP transcriptional activity during the course of brain development. However, few reports did demonstrate that systemic MPTP injection into neonatal mice resulted in permanent brain damages in adulthood, as measured (Ali et al., 1993, Fredriksson et al., 1993, Schwartz and Nishiyama, 1994). Nevertheless these early reports brought out the point that the developing brain is vulnerable to MPTP as well, and deserved a careful investigation. Therefore, the model described here offers several new opportunities to study neuronal degeneration in live animals. In this present invention, it is now possible to monitor the effects of various drugs to prevent neurodamage due to stroke and crush injuries in living animals. Furthermore, one could use this GFAP-GFP transgenic neonatal mouse to study GFAP up-regulation as it occurs in various models of Alzheimer's (Vanzani et al., 2005) and Huntington's disease (Ishiguro et al., 2001) and monitor non-invasively the neuroprotective effect of various drug treatments. In addition to neurodegeneration, these mice may be useful to study the development and treatment of brain tumors. A recent paper by Kalamarides et al. (Kalamarides et al., 2002) described a mouse meningioma model in which the Nf2 gene was inactivated in arachnoidal cells. GFAP expression was up-regulated in astrocytes surrounding the tumor as it invaded the brain tissue and grew (Pekny and Nilsson, 2005). A further advantage of the present invention is that no anesthetics were introduced to the neonatal pups so as to evade any possible neurotoxic effects on the mouse.

No obvious changes of TH-like immunoreactivity were detected in the SNC and the ventral tegmental area in the 2'-CH$_3$-MPTP-treated mice, suggesting that the degeneration of nigrostriatal dopamine neurons was still not apparent 6 hours after 2'-CH$_3$-MPTP injection. This is in good agreement with Araki et al.'s observation that the reduction of the dopaminergic neurons occurred 5 days after MPTP treatment (Araki et al., 2001) and Kurosaki et al.'s finding that TH immunopositive fibers and cell bodies were reduced in the striatum and substantia nigra only a day after MPTP treatment. Further studies focused on systemic administration of 2'-CH$_3$-MPTP and the effects on GFAP and TH immunostaining over a period of 24, 48 and 72 hours post-treatment will broaden our understanding in this field.

In addition to MPTP, a number of other chemicals have been reported to cause neuronal damages in various regions of adult mouse brain, as evidenced by GFAP elevation. These chemicals include a long list of structurally and functionally diverse compounds, ranging from industrial toxic compounds such as trimethylin (O'Callaghan, 1988) and methylmercury (O'Callaghan, 1988, Barone Jr. et al., 1998, Garcia et al., 2002), agricultural pesticides (Garcia et al., 2002), to food additives (Ostergren et al., 2005). Compared to the developed brain in adult, the developing brain with less intact blood-brain-barrier is much more vulnerable to damages caused by known neurotoxins, and more critically by numerous chemical compounds which could find their way into the human food chain and the environment without first being properly tested for their neurotoxicity. The importance of testing chemicals for their potential neurotoxicity in developing brain cannot be over emphasized (Olney, 2002), especially in dealing with the issue of silent neurotoxicity (Costa et al., 2004). This was further exacerbated by the US Environmental Protection Agency's Developmental Neurotoxicity Testing Guideline (DNTG) reviewed by (Tilson, 2000). More recently the European Commission adopting a proposal for a new European Union regulatory framework to test all chemicals through a rigorous regime with estimates of the new measure costing up to seven billion euros and taking at least ten years to implement (European, 2003). However it is a formidable challenge using the traditional GFAP techniques to try to assess a large number of chemicals for their neurotoxic risk to the developing CNS in vivo, especially when taking into the account that the assay method must offer a sound scientific ground at a reasonable throughput and cost acceptable to both industries (Kaufmann, 2003) and regulatory bodies (Hass, 2003).

With the integration of the proven GFAP-GFP transgenic mouse model (Zhuo et al., 1997), which displayed an exclusive glial expression pattern in all major regions of the brain (Su et al., 2004), to an appropriate in vivo optical bioimaging system, it is possible to study non-invasively neurodegeneration diseases, developmental neurotoxicology and to screen chemical compounds in a real-time manner, and potentially therapeutic interventions of other CNS pathologies such as wound healing after trauma, stroke and tumor growth.

REFERENCES

1. Abdel-Wahab, M. H., 2005. Potential neuroprotective effect of t-butylhydroquinone against neurotoxicity—induced by 1-methyl-4-(2'-methylphenyl)-1,2,3,6-tetrahydropyridine (2'-methyl-MPTP) in mice. Journal of Biochemical and Molecular Toxicology. 19, 32-41.
2. Ali, S. F., David, S. N. and Newport, G. D., 1993. Age-related susceptibility to MPTP-induced neurotoxicity in mice. Neurotoxicology. 14, 29-34.
3. Araki, T., Mikami, T., Tanji, H., Matsubara, M., Imai, Y., Mizugaki, M. and Itoyama, Y., 2001. Biochemical and immunohistological changes in the brain of 1-methyl-4-phenyl-1,2,3,6-tetrahydropyridine (MPTP)-treated mouse. European Journal of Pharmaceutical Sciences. 12, 231-238.
4. Barone Jr., S., Haykal-Coates, N., Parran, D. K. and Tilson, H. A., 1998. Gestational exposure to methylmercury alters the developmental pattern of trk-like immunoreactivity in the rat brain and results in cortical dysmorphology. Developmental Brain Research. 109, 13-31.
5. Bhaumik, S. and Gambhir, S. S., 2002. Optical imaging of renilla luciferase reporter gene expression in living mice. Proceeding of the National Academy of Sciences. 99, 337-382.
6. Bloem, B. R., Irwin, I., Buruma, O. J. S., Haan, J., Roos, R. A. C., Tetrud, J. W. and Langston, J. W., 1990. The MPTP model: versatile contributions to the treatment of idiopathic Parkinson's disease. Journal of Neurological Sciences. 97, 273-293.
7. Bouvet, M., Wang, J., Nardin, S. R., Nassirpour, R., Yang, M., Baranov, E., Jiang, P., Moossa, A. R. and Hoffman, R. M., 2002. Real-time optical imaging of primary tumor growth and multiple metastatic events in a pancreatic cancer orthotopic model. Cancer research. 62, 1534-1540.
8. Brenner, M., Kisserberth, W. C., Su, Y., Besnard, F. and A, M., 1994. GFAP promotor directs astrocyte-specific expression in transgenic mice. Journal of Neuroscience. 14, 1030-1037.
9. Chen, L. W., Wei, L. C., Qiu, Y., Liu, H. L., R, R. Z., Ju, G. and Chan, Y. S., 2002. Significant up-regulation of nestin protein in the neostriatum of MPTP-treated mice. Are the striatal astrocytes regionally activated after systemic MPTP administration? Brain Research. 925, 9-17.
10. Contag, C. H., Jenkins, D., Contag, P. R. and Negrin, R. S., 2000. Use of reporter genes for optical measurements of neoplastic disease in vivo. Neoplasia. 2, 41-52.
11. Costa, L. G., Aschner, M., Vitalone, A., Syversen, T. and Soldin, O. P., 2004. Developmental neuropathology of environmental agents. Annual Review of Pharmacology and Toxicology. 44, 87-110.
12. Damier, P., Hirsch, E. C., Agid, Y. and Graybiel, A. M., 1999. The substantia nigra of the human brain. II. Patterns of loss of dopamine-containing neurons in Parkinson's disease. Brain Research. 122, 1437-1448.
13. Dauer, W. and Przedborski, S., 2003. Parkinson's disease: mechanisms and models. Neuron. 39, 889-909.
14. Dervan, A. G., Meshul, C. K., Beales, M., McBean, G. J., Moore, C., Totterdell, S., Snyder, A. K. and Meredith, G. E., 2004. Astroglial plasticity and glutamate function in a chronic mouse model of Parkinson's disease. Experimental Neurology. 190, 145-156.
15. Eng, L. F., Ghirnikar, R. S. and Lee, Y. L., 2000. Glial Fibrillary Acidic Protein: GFAP Thirty-One Years (1969-2000)*. Neurochemical Research. 25, 1439-1451.
16. European, C., 2003. Proposal for a regulation of the European Parliament and of the council concerning the Registration, Evaluation, Authorisation and Restriction of Chemicals (REACH). COM 2003 0644 (03).
17. Fahn, S. and Przedborski, S., 2000. Merritt's neurology. Lippincott Williams and Wilkins, New York.
18. Fields, R. D. and Stevens-Graham, B., 2002. New insights into neuron-glia communication. Science. 298, 556-562.
19. Flint Beal, M., 2001. Experimental models of Parkinson's disease. Nature Reviews Neuroscience. 2, 325-332.
20. Franklin, K. and Paxinos, G., 2001. The Mouse Brain in Stereotaxic Coordinates. Academic Press.

21. Fredriksson, A., Fredriksson, M. and Eriksson, P., 1993. Neonatal exposure to paraquat or MPTP induces permanent changes in striatum dopamine and behavior in adult mice. Toxicology and Applied Pharmacology. 122, 258-264.
22. Garcia, S. J., Seidler, F. J., Qiao, D. and Slotkin, T. A., 2002. Chlorpyrifos targets developing glia: effects on glial fibrillary acidic protein. Developmental Brain Research. 133, 151-161.
23. German, D. C., Nelson, E. L., Liang, C. L., Speciale, S. G., Sinton, C. M. and Sonsalla, P. K., 1999. The neurotoxin MPTP causes degeneration of specific nucleus A8, A9 and A10 dopaminergic neurons in the mouse. Neurodegeneration. 5, 299-312.
24. Hass, U., 2003. Current status of developmental neurotoxicity: regulatory view. Toxicology Letters. 140-141, 155-159.
25. Hoffman, R. M., 2004. In vivo imaging with fluorescent proteins: the new cell biology. Acta Histochemica. 106, 77-87.
26. Ishiguro, H., Yamada, K., Sawada, H., Nishii, K., Ichino, N., Sawada, M., Kurosawa, Y., Matsushita, N., Kobayashi, K., Goto, J., Hashida, H., Masuda, N., Kanazawa, I. and Nagatsu, T., 2001. Age-dependent and tissue-specific CAG repeat instability occurs in mouse-knock-in for a mutant Huntington's disease gene. Journal of Neuroscience Research. 65, 289-297.
27. Kalamarides, M., Niwa-Kawakita, M., Leblois, H., Abramowski, V., Perricaudet, M., Janin, A., Thomas, G., Gutmann, D. H. and Giovannini, M., 2002. Nf2 gene inactivation in arachnoidal cells is rate-limiting for meningioma development in the mouse. Genes and development. 16, 1060-1065.
28. Kaufmann, W., 2003. Current status of developmental neurotoxicity: an industry perspective. Toxicology Letters. 140-141, 161-169.
29. Kurosaki, R., Muramatsu, Y., Kato, H. and Araki, T., 2004. Biochemical, behavioral and immunohistochemical alterations in MPTP-treated mouse model of Parkinson's disease. Pharmacology, Biochemistry and Behavior. 78, 143-153.
30. Luellen, B. A., Miller, D. B., Chisnell, A. C., Murphy, D. L., O'Callaghan, J. P. and Andrews, A. M., 2003. Neuronal and astroglial responses to the serotonin and norepinephrine neurotoxin: 1-methyl-4-(2'-aminophenyl)-1,2,3,6-tetrahydropyridine. Journal of Pharmacology and Experimental Therapeutics. 307, 923-931.
31. Ntziachristos, V., Tung, C. H., Bremer, C. and Weissleder, R., 2002. Fluorescence molecular tomography resolves protease activity in vivo. Nature Medicine. 8, 757-760.
32. O'Callaghan, J. P., 1988. Neurotypic and gliotypic proteins as biochemical markers of neurotoxicity. Neurotoxicology and Teratology. 10, 445-452.
33. O'Callaghan, J. P., 1991. Quantification of glial fibrillary acidic protein: comparison of slot-immunobinding assys with a novel sandwich ELISA. Neurotoxicology and Teratology. 13, 275-281.
34. Olanow, W. and Tatton, W. G., 1999. Etiology and pathogenesis of Parkinson's disease. Annual Review of Neuroscience. 22, 123-144.
35. Olney, J. W., 2002. New insights and new issues in developmental neurotoxicology. Neurotoxicology. 23, 659-668.
36. Ostergren, A., Fredriksson, A. and Brittebo, E. B., 2005. Norharman-induced motoric impairment in mice: neurodegeneration and glial activation in substantia nigra. Journal of Neural Transmission. Online publication ahead of print (3 Aug. 2005).
37. Pekny, M. and Nilsson, M., 2005. Astrocyte activation and reactive gliosis. Glia. 50, 427-434.
38. Rehemtulla, A., Stegman, L. D., Cardozo, S. J., Gupta, S., Hall, D. E., Contag, C. H. and Ross, B. D., 2000. Rapid and quantitative assessment of cancer treatment response using in vivo bioluminescence imaging. Neoplasia. 2, 491-495.
39. Reinhard, J. F. J., Miller, D. B. and O'Callaghan, J. P., 1988. The neurotoxicant MPTP (1-methyl-4-phenyl-1,2,3,6-tetrahydropyridine) increases glial fibrillary acidic protein and decreases dopamine levels of the mouse striatum: evidence for glial response to injury. Neuroscience Letters. 95, 246-251.
40. Scallet, A. C., Schmued, L. C., Slikker, W., Grunberg, N., Faustino, P. J., Davis, H., Lester, D., Pine, P. S., Sistare, F. and Hanig, J. P., 2004. Developmental neurotoxicity of ketamine: Morphometric confirmation, exposure parameters, and multiple fluorescent labeling of apoptotic neurons. Toxicological Sciences. 81, 364-370.
41. Schwartz, J. P. and Nishiyama, N., 1994. Neurotrophic factor gene expression in astrocytes during development and following injury. Brain Research Bulletin. 35, 403-407.
42. Su, M., Hu, H., Lee, Y., d'Azzo, A., Messing, A. and Brenner, M., 2004. Expression specificity of GFAP transgenes. Neurochemical Research. 29, 2075-2093.
43. Tanji, H., Araki, T., Nagasawa, H. and Itoyama, Y., 1999. Differential vulnerability of dopamine receptors in the mouse brain treated by MPTP. Brain Research. 824, 224-231.
44. Tatton, N. A. and Kish, S. J., 1997. In situ detection of apoptotic nuclei in the substantia nigra compacta of 1-methyl-4-phenyl-1,2,3,6-tetrahydropyridine-treated mice using terminal deoxynucleotidyl transferase labelling and acridine orange staining. Neuroscience. 77, 1037-1048.
45. Tilson, H. A., 2000. The role of developmental neurotoxicology studies in risk assessment. Toxicologic Pathology. 28, 149-156.
46. Troy, T., Jekic-McMullen, D., Sambucetti, L. and Rice, B., 2004. Quantitative comparison of the sensitivity of detection of fluorescent and bioluminescent reporters in animal models. Molecular Imaging. 3, 9-23.
47. Vanzani, M. C., Iacono, R. F., Caccuri, R. L. and Berria, M. I., 2005. Immunochemical and morphometric features of astrocyte reactivity vs. plaque location in Alzheimer's disease. Medicina-Buenos Aires. 65, 213-218.
48. Vila, M. and Przedborski, S., 2004. Genetic clues to the pathogenesis of Parkinson's disease. Nature Medicine. 10 (Suppl), S58-S62.
49. Yang, M., Baranov, E., Jiang, P., Sun, F. X., Li, X. M., Li, L., Hasegawa, S., Bouvet, M., Al-Tuwaijri, M., Chishima, T., Shimada, H., Moossa, A. R., Penman, S. and Hoffman, R. M., 2000. Whole body optical imaging of green fluorescent protein-expressing tumors and metastases. Proceeding of the National Academy of Sciences. 97, 1206-1211.
50. Zhang, W., Feng, Q. J., Harris, S. E., Contag, P. R., Stevenson, D. K. and Contag, C. H., 2001. Rapid in vivo functional analysis of transgenes in mice using whole body imaging of luciferase expression. Transgenic Research. 10, 423-434.
51. Zhu, L., Ramboz, S., Hewitt, D., Boring, L., Grass, D. S. and Purchio, A. F., 2004. Non-invasive imaging of GFAP expression after neuronal damage in mice. Neuroscience Letters. 367, 210-212.

52. Zhuo, L., Sun, B., Zhang, C. L., Fine, A., Chiu, S. Y. and Messing, A., 1997. Live astrocytes visualized by green fluorescent protein in transgenic mice. Developmental biology. 187, 36-42.

The invention claimed is:

1. A method of detecting the expression of a fluorescent protein of interest in the central nervous system of a mammal, wherein the central nervous system does not include the retina or cornea, and wherein the mammal is a transgenic mammal having in its genome nucleic acid encoding said fluorescent protein operably linked to a glial fibrillary acidic protein (GFAP) promoter, the method comprising the step of non-invasively detecting fluorescence from said fluorescent protein when expressed in said mammal, wherein said mammal is a neonate.

2. The method of claim 1 wherein said fluorescent protein is a green fluorescent protein (GFP).

3. The method of claim 1 wherein the method is for studying the effect of administration of a test substance to said mammal, the method comprising the step of administering said test substance to said mammal prior to the step of non-invasive detection of fluorescence.

4. The method of claim 3 wherein the method comprises the step of comparing fluorescence from a control mammal in the absence of administration of said test substance with the fluorescence from said transgenic mammal following administration of said test substance to the transgenic mammal.

5. The method of claim 3 wherein the method comprises the steps of:
 (i) non-invasively detecting fluorescence in said transgenic mammal before administration of the test substance to provide a control;
 (ii) non-invasively detecting fluorescence in the same mammal after administration of the test substance; and
 (iii) comparing the fluorescence detected in (i) with the fluorescence detected in (ii).

6. The method of claim 3 wherein the method comprises the steps of:
 (i) non-invasively detecting fluorescence in a first mammal to provide a control;
 (ii) administering a test substance to a second transgenic mammal followed by non-invasively detecting fluorescence in that mammal; and
 (iii) comparing the fluorescence detected in (i) with the fluorescence detected in (ii).

7. The method of claim 3 wherein the method is for determining the neurotoxicity of the test substance.

8. The method of claim 1 wherein the method is for testing the ability of a test substance to facilitate treatment of, or to modulate, neurological damage wherein the method comprises the steps of:
 (i) inducing neurological damage in said transgenic mammal;
 (ii) non-invasively detecting fluorescence in said neurologically damaged mammal from (i) prior to administration of the test substance to provide a control;
 (iii) non-invasively detecting fluorescence in the same mammal from (ii) after administration of the test substance; and
 (iv) comparing the fluorescence detected in (ii) with the fluorescence detected in (iii).

9. The method of claim 1 wherein the method is for testing the ability of a test substance to facilitate treatment of, or to modulate, neurological damage wherein the method comprises the steps of:
 (i) inducing neurological damage in a first mammal and non-invasively detecting fluorescence in the neurologically damaged mammal to provide a control;
 (ii) inducing neurological damage in a second transgenic mammal and administering the test substance to that mammal followed by non-invasively detecting fluorescence in that mammal; and
 (iii) comparing the fluorescence detected in (i) with the fluorescence detected in (ii).

10. The method of claim 8 or 9 wherein the neurological damage is induced by administration of a selected chemical to the mammal.

11. The method of claim 10 wherein the chemical is administered so as to provide a chemically induced animal model of a selected disease.

12. The method of claim 11 wherein the disease is chosen from Parkinson's Disease, Alzheimer's Disease or Huntington's Disease.

13. The method of claim 10 wherein the chemical is chosen from MPTP, 2'-$CH_3$-MPTP, 6-hydroxydopamine (6-OHDA), Kainic acid, Trimethylin, Chlorpyrifos (CPF), Manganese-ethylenebisdithiocarbamate (Maneb or MB), rotenone, Paraquat (N,N',-dimethyl-4-4'-bipiridinium), Polychlorinated biphenyls (PCBs), 3,3'-lminodipropionitrile (IDPN), Toluene (methylbenzene).

14. The method of claim 8 or 9 wherein the neurological damage is induced by physical force applied to the head and/or neck and/or back of the mammal.

15. The method of claim 8 or 9 wherein the neurological damage is induced by decreasing the supply of oxygen to the mammal's nervous system leading to cerebral ischaemia.

16. The method of claim 1 wherein the method is for testing the ability of a test substance to facilitate treatment of a nervous system disease wherein the method comprises the steps of:
 (i) providing said transgenic mammal, wherein the mammal is also an animal model of said nervous system disease;
 (ii) non-invasively detecting fluorescence in said mammal from (i) prior to administration of the test substance to provide a control;
 (iii) non-invasively detecting fluorescence in the same mammal from (ii) after administration of the test substance; and
 (iv) comparing the fluorescence detected in (ii) with the fluorescence detected in (iii).

17. The method of claim 1 wherein the method is for testing the ability of a test substance to facilitate treatment of a nervous system disease wherein the method comprises the steps of:
 (i) providing first and second mammals, wherein both mammals are animal models of said nervous system disease;
 (ii) in a first mammal from (i) non-invasively detecting fluorescence in the mammal to provide a control;
 (iii) in a second transgenic mammal from (i) administering the test substance to that mammal followed by non-invasively detecting fluorescence in that mammal; and
 (iv) comparing the fluorescence detected in (ii) with the fluorescence detected in (iii).

18. The method of claim 1 wherein the method is for testing a treatment for a nervous system disease wherein the method comprises the steps of:
 (i) providing said transgenic mammal, wherein the mammal is also an animal model of said nervous system disease;

(ii) non-invasively detecting fluorescence in said mammal from (i) prior to applying the treatment to provide a control;
(iii) non-invasively detecting fluorescence in the same mammal from (ii) after applying the treatment; and
(iv) comparing the fluorescence detected in (ii) with the fluorescence detected in (iii).

19. The method of claim 3 wherein the method is for testing a treatment for a nervous system disease wherein the method comprises the steps of:
(i) providing first and second mammals, wherein both mammals are animal models of said nervous system disease;
(ii) in a first mammal from (i) non-invasively detecting fluorescence in the mammal to provide a control;
(iii) in a second transgenic mammal from (i) applying the treatment to that mammal followed by non-invasively detecting fluorescence in that mammal; and
(iv) comparing the fluorescence detected in (ii) with the fluorescence detected in (iii).

20. The method of claim 18 or 19 wherein the treatment involves the application of X-rays or γ-rays.

21. The method of any one of claims 16 to 19 wherein the nervous system disease is a nervous system tumor.

22. The method of claim 21 wherein the tumor is chosen from glioma, medulloblastoma, meningioma, neurofibroma, ependymoma, Schwannoma, neurofibrosarcoma, astrocytoma, oligodendroglioma.

* * * * *